US012712062B2

(12) United States Patent
Peake et al.

(10) Patent No.: US 12,712,062 B2
(45) Date of Patent: Aug. 18, 2026

(54) STORING, CONTROLLING, AND PORTING RESPIRATORY SETTINGS FROM A REMOTE SERVER

(71) Applicant: ResMed Inc., San Diego, CA (US)

(72) Inventors: Gregory Robert Peake, Sydney (AU); Ryan Mathew Hernandez, Encinitas, CA (US)

(73) Assignee: ResMed Inc., San Diego, CA (US)

( * ) Notice: Subject to any disclaimer, the term of this patent is extended or adjusted under 35 U.S.C. 154(b) by 1317 days.

(21) Appl. No.: 17/599,470

(22) PCT Filed: Mar. 27, 2020

(86) PCT No.: PCT/US2020/025493
§ 371 (c)(1),
(2) Date: Sep. 28, 2021

(87) PCT Pub. No.: WO2020/205641
PCT Pub. Date: Oct. 8, 2020

(65) Prior Publication Data

US 2022/0189609 A1 Jun. 16, 2022

Related U.S. Application Data

(60) Provisional application No. 62/826,350, filed on Mar. 29, 2019.

(51) Int. Cl.
*G16H 20/40* (2018.01)
*A61M 16/00* (2006.01)
(Continued)

(52) U.S. Cl.
CPC ........ *G16H 20/40* (2018.01); *A61M 16/0003* (2014.02); *A61M 16/024* (2017.08);
(Continued)

(58) Field of Classification Search
CPC ......... G16H 20/40; G16H 20/10; G16H 40/63
See application file for complete search history.

(56) References Cited

U.S. PATENT DOCUMENTS 7,225,809 B1 6/2007 Bowen et al.
11,116,924 B2 9/2021 Delangre et al.
(Continued)

FOREIGN PATENT DOCUMENTS

CN 1474992 A 2/2004
CN 101874734 A 11/2010
(Continued)

OTHER PUBLICATIONS

International Search Report in International Patent Application No. PCT/US2020/025493 mailed Aug. 6, 2020 (4 pp.).
(Continued)

*Primary Examiner* — Brandy S Lee
*Assistant Examiner* — Mishal Zahra Hussain
(74) *Attorney, Agent, or Firm* — Nixon Peabody LLP

(57) ABSTRACT

Disclosed are systems and methods for automatically porting respiratory therapy settings to a new respiratory therapy device. Currently, when a patient replaces receives a replacement respiratory therapy device, the prescription settings must be manually ported. Accordingly, the inventors have developed technology to automatically, port, translate, and validate therapy settings and modes to a replacement respiratory therapy device.

29 Claims, 18 Drawing Sheets

(51) Int. Cl.

| | |
|---|---|
| ***G06F 16/245*** | (2019.01) |
| ***G16H 40/63*** | (2018.01) |
| ***G16H 40/67*** | (2018.01) |
| ***G16H 50/30*** | (2018.01) |

(52) U.S. Cl.

CPC ........... *G06F 16/245* (2019.01); *G16H 40/63* (2018.01); *G16H 40/67* (2018.01); *G16H 50/30* (2018.01); *A61M 2205/3334* (2013.01); *A61M 2205/3368* (2013.01); *A61M 2205/3584* (2013.01); *A61M 2205/502* (2013.01); *A61M 2205/52* (2013.01); *A61M 2205/609* (2013.01); *A61M 2205/84* (2013.01); *A61M 2209/01* (2013.01); *A61M 2230/04* (2013.01); *A61M 2230/205* (2013.01)

(56) References Cited

U.S. PATENT DOCUMENTS

| | | | | |
|---|---|---|---|---|
| 11,596,754 | B2 * | 3/2023 | Hickey | H04W 12/06 |
| 2002/0077856 | A1 * | 6/2002 | Pawlikowski | G16H 40/40 705/2 |
| 2007/0156193 | A1 | 7/2007 | Cho et al. | |
| 2007/0209662 | A1 * | 9/2007 | Bowen | A61M 16/0063 128/204.21 |
| 2009/0234240 | A1 | 9/2009 | Kuenzler et al. | |
| 2010/0059057 | A1 * | 3/2010 | Tapppehoon | A61M 16/08 128/204.18 |
| 2010/0285821 | A1 * | 11/2010 | Smeeding | G06Q 30/02 705/14.34 |
| 2013/0104893 | A1 * | 5/2013 | Steinhauer | A61M 16/0051 128/204.21 |
| 2014/0150791 | A1 * | 6/2014 | Birnkrant | G16H 20/40 128/204.23 |
| 2015/0154364 | A1 * | 6/2015 | Biasi | A61B 5/11 709/223 |
| 2015/0199479 | A1 | 7/2015 | Semen et al. | |
| 2016/0058967 | A1 * | 3/2016 | McCormick | A61M 16/0883 128/205.24 |
| 2016/0239626 | A1 * | 8/2016 | Buckley | G16H 10/60 |
| 2017/0043089 | A1 * | 2/2017 | Handler | G16H 20/17 |
| 2017/0136198 | A1 * | 5/2017 | Delangre | A61M 16/0051 |
| 2017/0209657 | A1 | 7/2017 | Levings et al. | |
| 2017/0311879 | A1 | 11/2017 | Armitstead et al. | |
| 2018/0182473 | A1 * | 6/2018 | Schwaibold | G16H 20/30 |
| 2019/0209806 | A1 * | 7/2019 | Allen | H04L 12/2829 |
| 2020/0297955 | A1 * | 9/2020 | Shouldice | A61M 16/06 |

FOREIGN PATENT DOCUMENTS

| | | | |
|---|---|---|---|
| CN | 107530514 | A | 1/2018 |
| CN | 108025132 | A | 5/2018 |
| CN | 108135534 | A | 6/2018 |
| CN | 108236749 | A | 7/2018 |
| CN | 108283749 | A | 7/2018 |
| EP | 2181726 | A1 | 5/2010 |
| EP | 3092021 | A1 | 11/2016 |
| EP | 3149696 | A1 | 4/2017 |
| JP | 2003527160 | A | 9/2003 |
| JP | 2017519292 | A | 7/2017 |
| WO | 2012/171072 | A1 | 12/2012 |
| WO | 2012168848 | A1 | 12/2012 |
| WO | 2018/151778 | A1 | 8/2018 |

OTHER PUBLICATIONS

Written Opinion in International Patent Application No. PCT/US2020/025493 mailed Aug. 6, 2020 (7 pp.).

* cited by examiner

Copyright 2012 ResMed Limited 1000
2000
2010
2020
2015
2030
2035
2050
2025
2060
2040
2045
2055

STORING, CONTROLLING, AND PORTING RESPIRATORY SETTINGS FROM A REMOTE SERVER

CROSS-REFERENCE TO RELATED APPLICATIONS

This application is the U.S. National Stage of International Patent Application No. PCT/US2020/025493, filed Mar. 27, 2020, which claims priority to and the benefit of U.S. Provisional Patent Application No. 62/826,350, filed Mar. 29, 2019, each of which is hereby incorporated by reference herein in its entirety.

1 BACKGROUND OF THE TECHNOLOGY

1.1 Field of the Technology

The present technology relates to one or more of the screening, diagnosis, monitoring, treatment, prevention and amelioration of respiratory-related disorders. The present technology also relates to medical devices or apparatus, and their use. The present technology also relates to porting respiratory settings between respiratory therapy devices.

1.2 Description of the Related Art 1.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

1.2.2 Therapies

Various therapies, such as Continuous Positive Airway Pressure (CPAP) therapy, Non-invasive ventilation (MV) and Invasive ventilation (IV) have been used to treat one or more of the above respiratory disorders.

1.2.2.1 Respiratory Pressure Therapies

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

1.2.2.2 Flow Therapies

Not all respiratory therapies aim to deliver a prescribed therapy pressure. Some respiratory therapies aim to deliver a prescribed respiratory volume, possibly by targeting a flow rate profile over a targeted duration. In other cases, the interface to the patient's airways is 'open' (unsealed) and the respiratory therapy may only supplement the patient's own spontaneous breathing. In one example, High Flow therapy (HFT) is the provision of a continuous, heated, humidified flow of air to an entrance to the airway through an unsealed or open patient interface at a "treatment flow rate" that is held approximately constant throughout the respiratory cycle. The treatment flow rate is nominally set to exceed the patient's peak inspiratory flow rate. HFT has been used to treat OSA, CSR, COPD and other respiratory disorders. One mechanism of action is that the high flow rate of air at the airway entrance improves ventilation efficiency by flushing, or washing out, expired CO2 from the patient's anatomical deadspace. HFT is thus sometimes referred to as a deadspace therapy (DST). In other flow therapies, the treatment flow rate may follow a profile that varies over the respiratory cycle.

Another form of flow therapy is long-term oxygen therapy (LTOT) or supplemental oxygen therapy. Doctors may prescribe a continuous flow of oxygen enriched gas at a specified oxygen concentration (from 21%, the oxygen fraction in ambient air, to 100%) at a specified flow rate (e.g., 1 litre per minute (LPM), 2 LPM, 3 LPM, etc.) to be delivered to the patient's airway.

1.2.2.3 Supplementary Oxygen

For certain patients, oxygen therapy may be combined with a respiratory pressure therapy or HFT by adding supplementary oxygen to the pressurised flow of air. When oxygen is added to respiratory pressure therapy, this is referred to as RPT with supplementary oxygen. When oxygen is added to HFT, the resulting therapy is referred to as RFT with supplementary oxygen.

1.2.3 Treatment Systems

These respiratory therapies may be provided by a therapy system or device. Such systems and devices may also be used to screen, diagnose, or monitor a condition without treating it.

A respiratory therapy system may comprise a Respiratory Pressure Therapy Device (RPT device), an air circuit, a humidifier, a patient interface, an oxygen source, and data management.

1.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$.

1.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus RPT devices may also act as flow therapy devices. Examples of RPT devices include CPAP devices and ventilators. Examples of RPT devices include a CPAP device and a ventilator.

1.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

1.2.3.4 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patients therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

1.2.3.5 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

1.2.3.6 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

1.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home screening/diagnosis/monitoring of sleep disordered breathing.

Screening and diagnosis generally describe the identification of a condition from its signs and symptoms. Screening typically gives a true/false result indicating whether or not a patient's SDB is severe enough to warrant further investigation, while diagnosis may result in clinically actionable information. Screening and diagnosis tend to be one-off processes, whereas monitoring the progress of a condition can continue indefinitely. Some screening/diagnosis systems are suitable only for screening/diagnosis, whereas some may also be used for monitoring.

Clinical experts may be able to screen, diagnose, or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

2 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

One form of the present technology comprises methods and systems for automatically porting respiratory therapy settings for a new respiratory therapy device. Currently, when a patient receives a replacement respiratory therapy device, an upgraded respiratory therapy device, or an additional or new type of respiratory therapy device, the prescription settings must be manually ported, with human intervention.

For instance, to acquire a new device when a patient already has an existing device and prescription (REPAP), the patient must order the new device from a provider, which must install the settings or the provider may manually update their cloud based database to add the new device and confirm the prescription for that patient is still valid. Therefore, generally a patient is limited to ordering a new device from a current provider in the possession of their prescription information, without facing difficulties or an extended installation process.

Another aspect of one form of the present technology is that it allows the system to check therapy quality indicators, such as oximetry readings to determine whether the therapy prescription settings should be automatically ported. For instance, automatically porting therapy settings presents challenges including that a patient may have a sub-optimal prescription that should not be ported because of low therapy quality. Therefore, systems and methods are disclosed for automatically checking and determining whether a prescription is effective for the patient, including by checking therapy quality indicators and effectiveness indicators that are disclosed herein.

Another aspect of one form of the present technology are features that check the date of the prescription, translate the settings between ventilator types, check for changes in patient information, or other relevant factors before automatically porting the prescription. As described herein, automatically porting the prescription therapy settings may have issues when two different types of models are being used. Accordingly, systems and methods are disclosed for translating the therapy settings herein.

Another aspect of one form of the present technology is the methods for automatically determining a patient status change that requires a prescription to be updated that includes but is not limited to weight, age, BMI, facial changes through image recognition software indicating a change, voice changes through audio analysis or other relevant patient changes that can be automatically detected or detect through administration of a questionnaire.

Another aspect of one form of the present technology is a patient interface that is moulded or otherwise constructed with a perimeter shape which is complementary to that of an intended wearer.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

Another aspect of the present technology may include a prescription database with prescription therapy settings referenced to patient account IDs comprising a unique identifier for each patient in the database in communication with a prescription server, a first respiratory therapy device, a second respiratory therapy device, an interface, a memory containing machine readable medium comprising machine executable code having stored thereon instructions for performing a method, a control system coupled to the memory comprising one or more processors, the control system configured to execute the machine executable code to cause the control system to receive input, from the interface, indicating a patient would like to port settings from the first respiratory therapy device; receiving, through the interface, an account ID associated with the patient and a hardware identifier with the first respiratory therapy device; and sending, to the prescription server, a request comprising the account ID and the hardware identifier to retrieve prescription therapy settings from the prescription server; receiving, from the prescription server, prescription therapy settings referenced to the account ID if the hardware identifier is validated; and storing the prescription therapy settings in a memory of the second respiratory therapy device.

Another aspect of the present technology includes where prescription therapy settings further comprises: retrieving a respiratory quality indicator referenced to the account ID based on respiratory therapy data output from the first respiratory device; determining whether the respiratory quality indicator is above a threshold; and flagging the patient for follow up and denying the request to port the prescription therapy settings if the respiratory quality indicator is below the threshold.

Another aspect of the present technology includes the respiratory quality indicator is an apnoea hypopnea index. Another aspect of the present technology includes wherein receiving, from the prescription server, prescription therapy settings further comprises: determining a time window that has expired since the prescription therapy settings were last updated; determining whether the time window is above a threshold; and flagging the patient for follow up and denying the request to port the prescription therapy settings if the time window is above the threshold.

Another aspect of the present technology includes where prescription therapy settings further comprises requesting a set of information from the patient; evaluating the information to determine whether a significant change has occurred relevant to the patient prescription therapy settings; and flagging the patient for follow up and denying the request to port the prescription therapy settings if the significant change has occurred.

Another aspect of the present technology includes where the set of information comprises at least one of: weight, BMI, muscle tone changes. Another aspect of the present technology includes wherein receiving, from the prescription server, prescription therapy settings further comprises: requesting a set of oximeter data output from a pulse oximeter; processing the oximeter data to determine whether the prescription therapy settings should be updated; and flagging the patient for follow-up in the prescription therapy database and denying the request to port the prescription therapy settings if the settings should not be updated.

Another aspect of the present technology includes where the set of information comprises audio data received through a microphone, and wherein the audio data is processed to determine whether the patient has a significant change in tone. Another aspect of the present technology includes wherein the set of information comprises image data of the face that is compared to previously captured image data to identify a significant facial change. Another aspect of the present technology includes wherein the significant facial change indicates a significant change in BMI.

Another aspect of the present technology includes the prescription therapy settings are received over a cellular antenna connected to the first respiratory therapy device.

Another aspect of the present technology includes wherein the prescription therapy settings are received over a Bluetooth or Wi-Fi connection to a mobile device connected to the first respiratory therapy device and wherein the prescription therapy settings are encrypted from the prescription server to the first respiratory therapy device.

Another aspect of the present technology includes wherein the prescription therapy settings comprise minimum and maximum pressure and therapy mode and the general therapy settings comprise humidity, RAMP, EPR, or therapy modes including CPAP, APA, Bi-Level and others.

Another aspect of the present technology includes wherein receiving, through the interface, an account ID associated with the patient's account and a serial number associated with the second respiratory therapy device, further comprises: displaying a code on a display of the first respiratory therapy device; requesting, on the interface, the code to be entered; and only receiving the general and prescription therapy settings of the code is validated.

Another aspect of the present technology includes wherein receiving the prescription therapy settings further comprises translating the prescription therapy settings by a predetermined translation factor based on a difference between the first and second respiratory therapy device.

Another aspect of the present technology includes A system comprising: a prescription database with prescription therapy settings referenced to patient prescription IDs comprising a unique identifier for each patient in the database in communication with a prescription server; a patient database with general patient data referenced to a set of patient account IDs in communication with a patient server; a first respiratory therapy device; an interface; a memory containing machine readable medium comprising machine executable code having stored thereon instructions for performing a method; a control system coupled to the memory comprising one or more processors, the control system configured to execute the machine executable code to cause the control system to: receive input, from the interface, indicating a patient would like to port settings from a second respiratory therapy device; receiving, through the interface, an account ID associated with the patient and a serial number associated with the second respiratory therapy device; and sending, to the patient server, a request comprising the account ID and the serial number to retrieve prescription therapy settings from the prescription server; receiving, from the patient server, prescription therapy settings referenced to a prescription ID that is referenced to the account ID if the serial number is validated set from the prescription server; and storing the prescription therapy settings in a memory of the second respiratory therapy device.

Another aspect of the present technology includes a method comprising: receiving input, from an interface, indicating a patient would like to port prescription therapy settings to a respiratory therapy device; receiving, from the interface, an account ID associated with the patient and a serial number associated with the respiratory therapy device; sending, to a prescription server, a request comprising the account ID and the serial number to retrieve prescription therapy settings from the prescription server; receiving, from the prescription server, prescription therapy settings referenced to the account ID if the serial number is validated; and storing the prescription therapy settings in a memory of the respiratory therapy device.

Another aspect of the present technology includes wherein storing the prescription therapy settings in a memory of the respiratory therapy device further comprises storing the prescription therapy settings for a single usage session. The method of claim 19, wherein storing the prescription therapy settings in a memory of the respiratory therapy device further comprises storing the prescription therapy settings for a single usage session.

Another aspect of the present technology includes wherein a single usage session comprises deleting the prescription therapy settings in the memory of the respiratory therapy device after a certain time window has expired.

Another aspect of the present technology includes wherein a single usage session comprises deleting the prescription therapy settings in the memory of the respiratory therapy device after the respiratory therapy device has been powered off.

Another aspect of the present technology includes a single usage session comprises deleting the prescription therapy settings in the memory of the respiratory therapy device after 24 hours, or deleting the prescription therapy settings in the memory of the respiratory therapy device after a notification that the patient has checked out of an associated hotel Another aspect of the present technology includes a method comprising: receiving, at a prescription server from a patient computing device, a request to port prescription therapy settings to a respiratory therapy device comprising an account ID associated with the patient and a serial number associated with the respiratory therapy device; querying, with the prescription server, a prescription database for the account ID and the serial number to retrieve a set of prescription therapy settings from the prescription database;

processing, with the prescription server, the serial number to determine whether it is validly associated with the account ID; and sending, to the respiratory therapy device, the set of prescription therapy settings referenced to the account ID if the serial number is validated.

Another aspect of the present technology includes a system comprising: a prescription database with prescription therapy settings referenced to patient account IDs comprising a unique identifier for each patient in the database in communication with a prescription server; an interface; an input module to receive input, from the interface, indicating a patient would like to port settings from a first respiratory therapy device; a receiving interface module for receiving, through the interface, an account ID associated with the patient and a hardware identifier with the first respiratory therapy device; a sending module for sending, to the prescription server, a request comprising the account ID and the hardware identifier to retrieve prescription therapy settings from the prescription server; a receiving server module for receiving, from the prescription server, prescription therapy settings referenced to the account ID if the hardware identifier is validated; and a storing module for storing the prescription therapy settings in a memory of the second respiratory therapy device.

Another aspect of the present technology includes A system comprising: a prescription database with prescription therapy settings referenced to patient prescription IDs comprising a unique identifier for each patient in the database in communication with a prescription server; a patient database with general patient data referenced to a set of patient account IDs in communication with a patient server; an interface; an input module to receive input, from the interface, indicating a patient would like to port settings from a second respiratory therapy device; an receiving interface module for receiving, through the interface, an account ID associated with the patient and a serial number associated with the second respiratory therapy device; and a sending module for sending, to the patient server, a request comprising the account ID and the serial number to retrieve prescription therapy settings from the prescription server; a receiving server module for receiving, from the patient server, prescription therapy settings referenced to a prescription ID that is referenced to the account ID if the serial number is validated set from the prescription server; and a storing module for storing the prescription therapy settings in a memory of the second respiratory therapy device.

Another aspect of the present technology includes a computer program product comprising instructions which, when the program is executed by a computer, cause the computer to carry out the steps of one of the methods above.

3 BRIEF DESCRIPTION OF THE DRAWINGS

The present technology is illustrated by way of example, and not by way of limitation, in the figures of the accompanying drawings, in which like reference numerals refer to similar elements including:

3.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

3.2 Respiratory System and Facial Anatomy

FIG. 2A shows an overview of a human respiratory system including the nasal and oral cavities, the larynx, vocal folds, oesophagus, trachea, bronchus, lung, alveolar sacs, heart and diaphragm.

3.3 Patient Interface

FIG. 3A shows a patient interface in the form of a nasal mask in accordance with one form of the present technology.

3.4 RPT Device

FIG. 4A shows an RPT device in accordance with one form of the present technology.

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

3.5 Humidifier

Figure 5A:
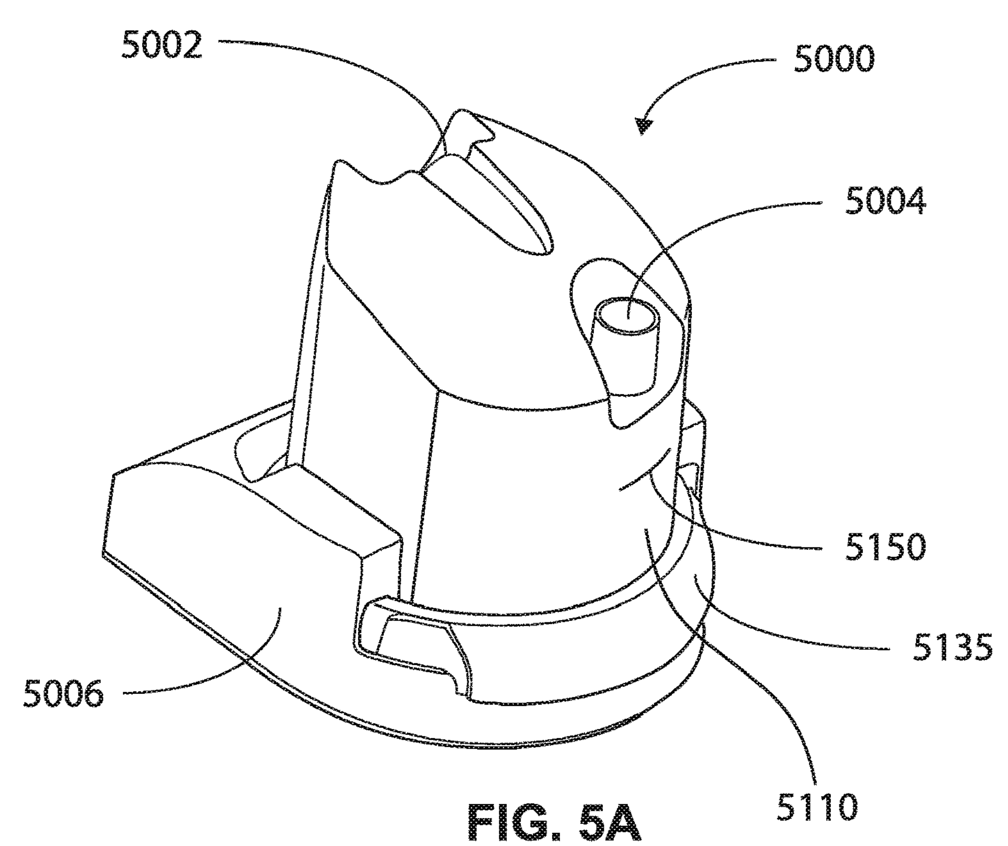

FIG. 5A shows an isometric view of a humidifier in accordance with one form of the present technology.

Figure 5B:
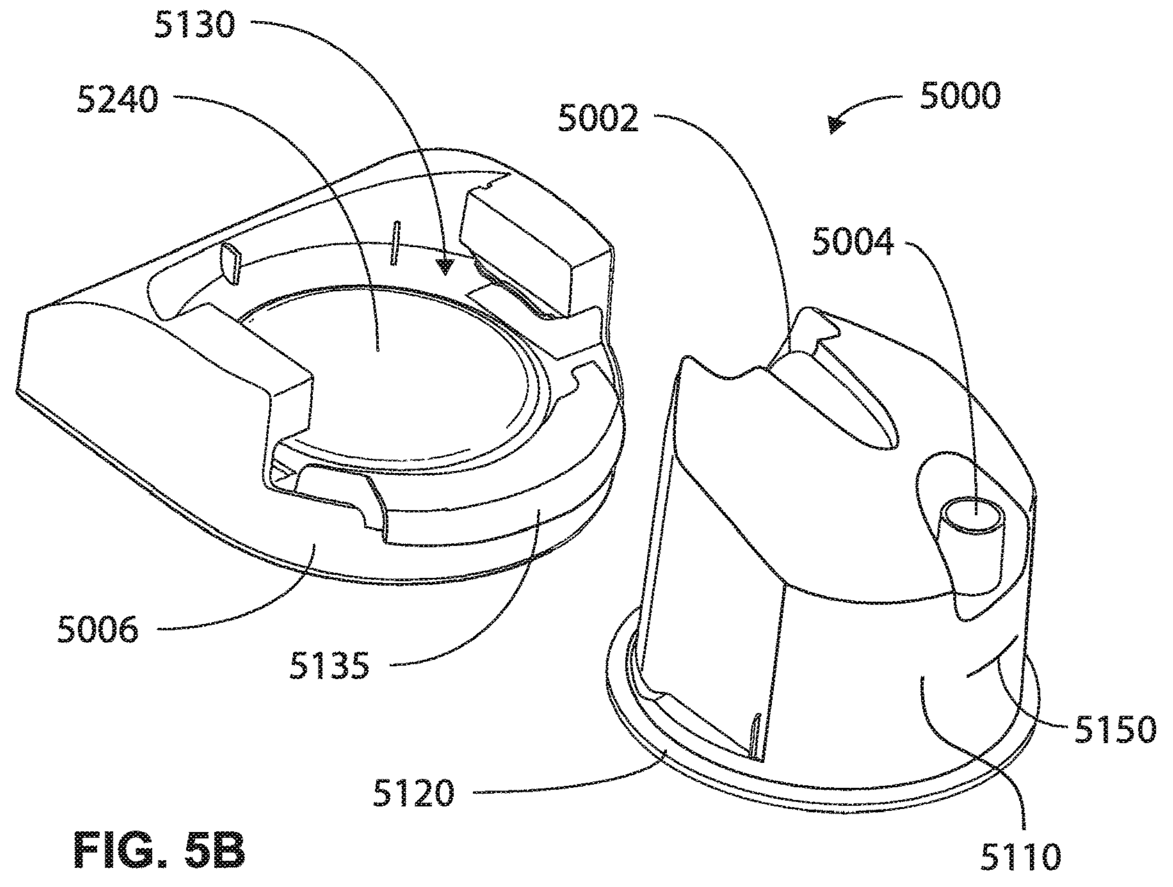

FIG. 5B shows an isometric view of a humidifier in accordance with one form of the present technology, showing a humidifier reservoir 5110 removed from the humidifier reservoir dock 5130.

3.6 Breathing Waveforms

Figure 6A:
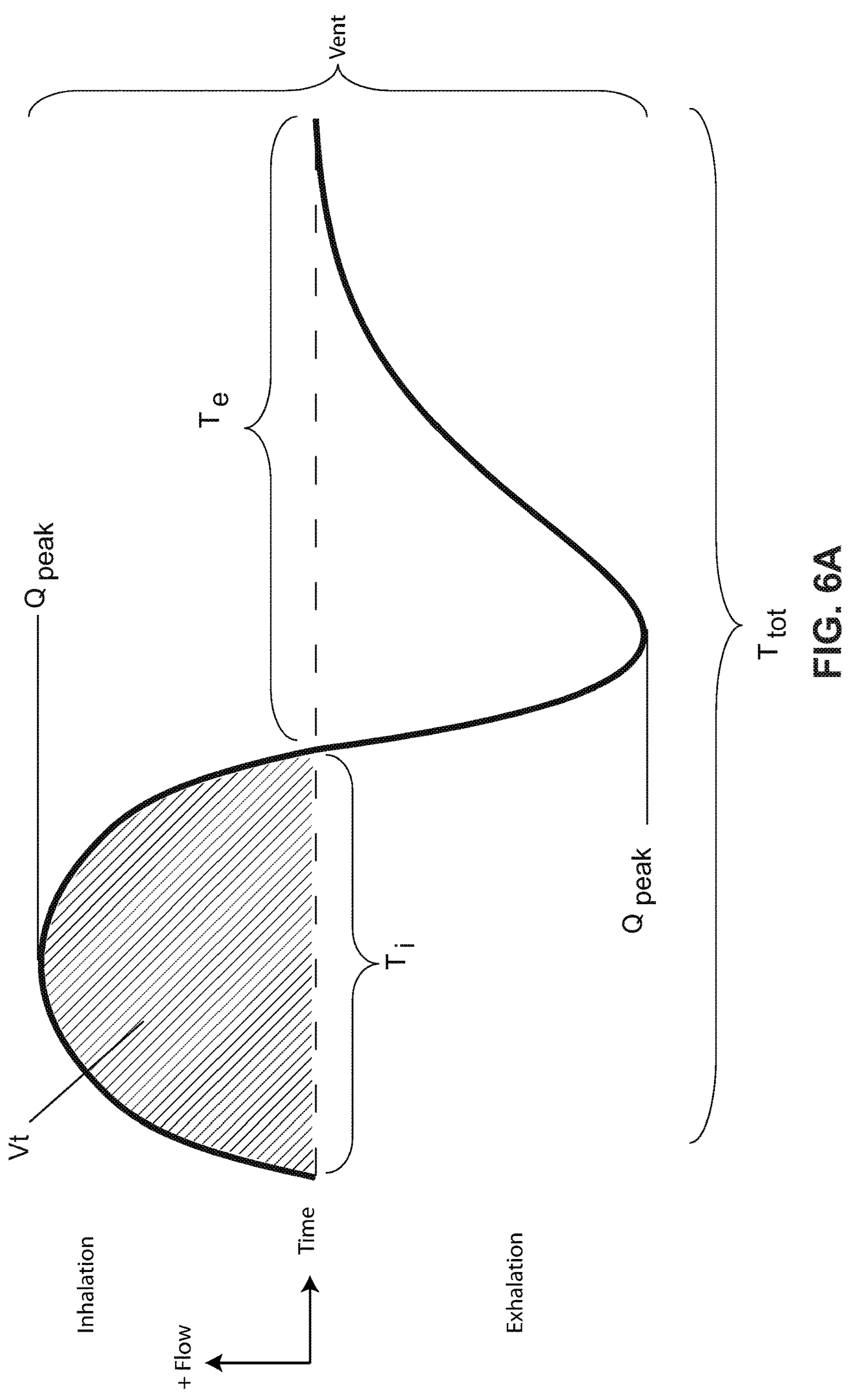

FIG. 6A shows a model typical breath waveform of a person while sleeping.

3.7 Screening, Diagnosis and Monitoring Systems

Figure 7A:
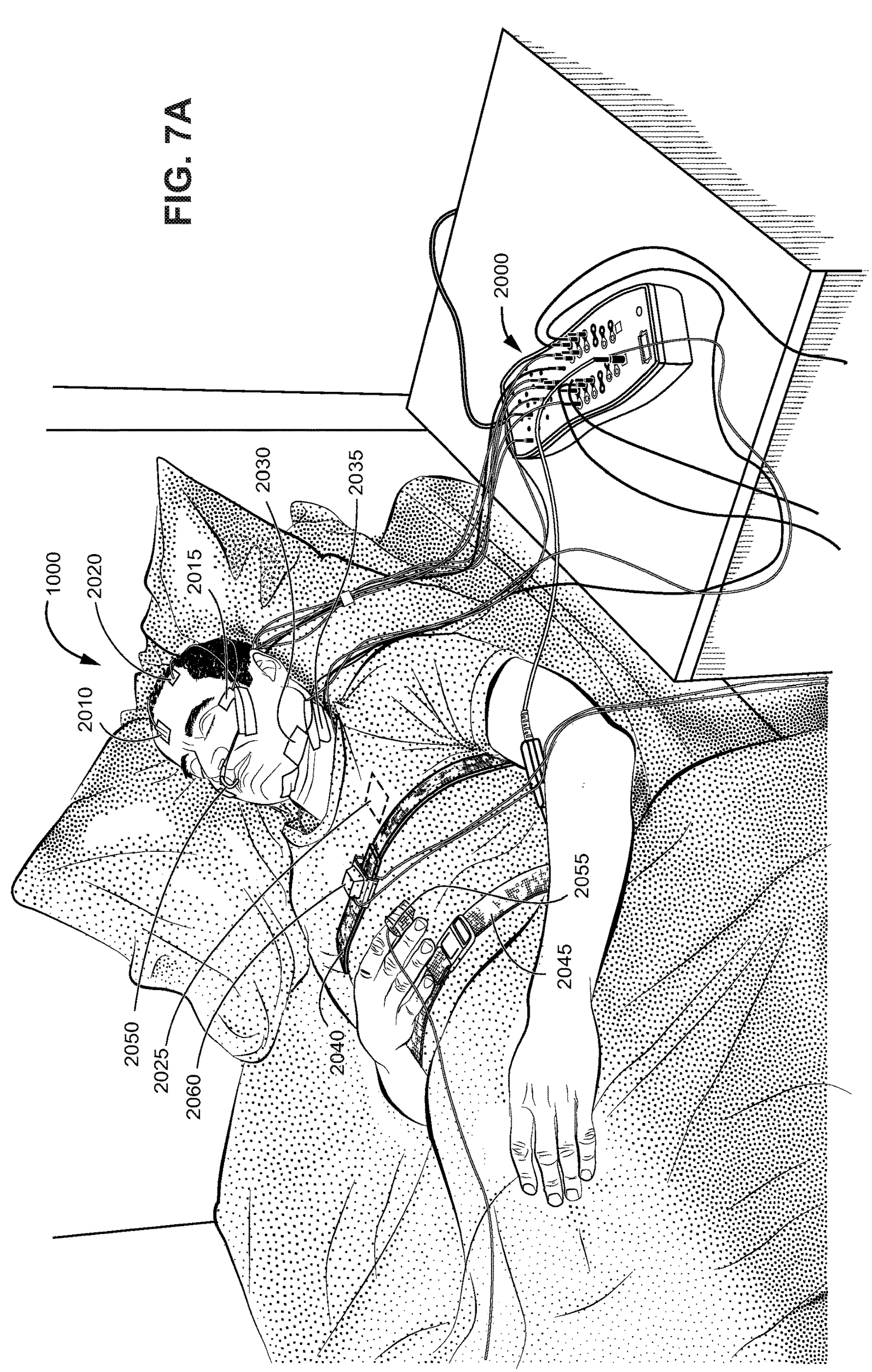

FIG. 7A shows a patient undergoing polysomnography (PSG). The patient is sleeping in a supine sleeping position.

Figure 7B:
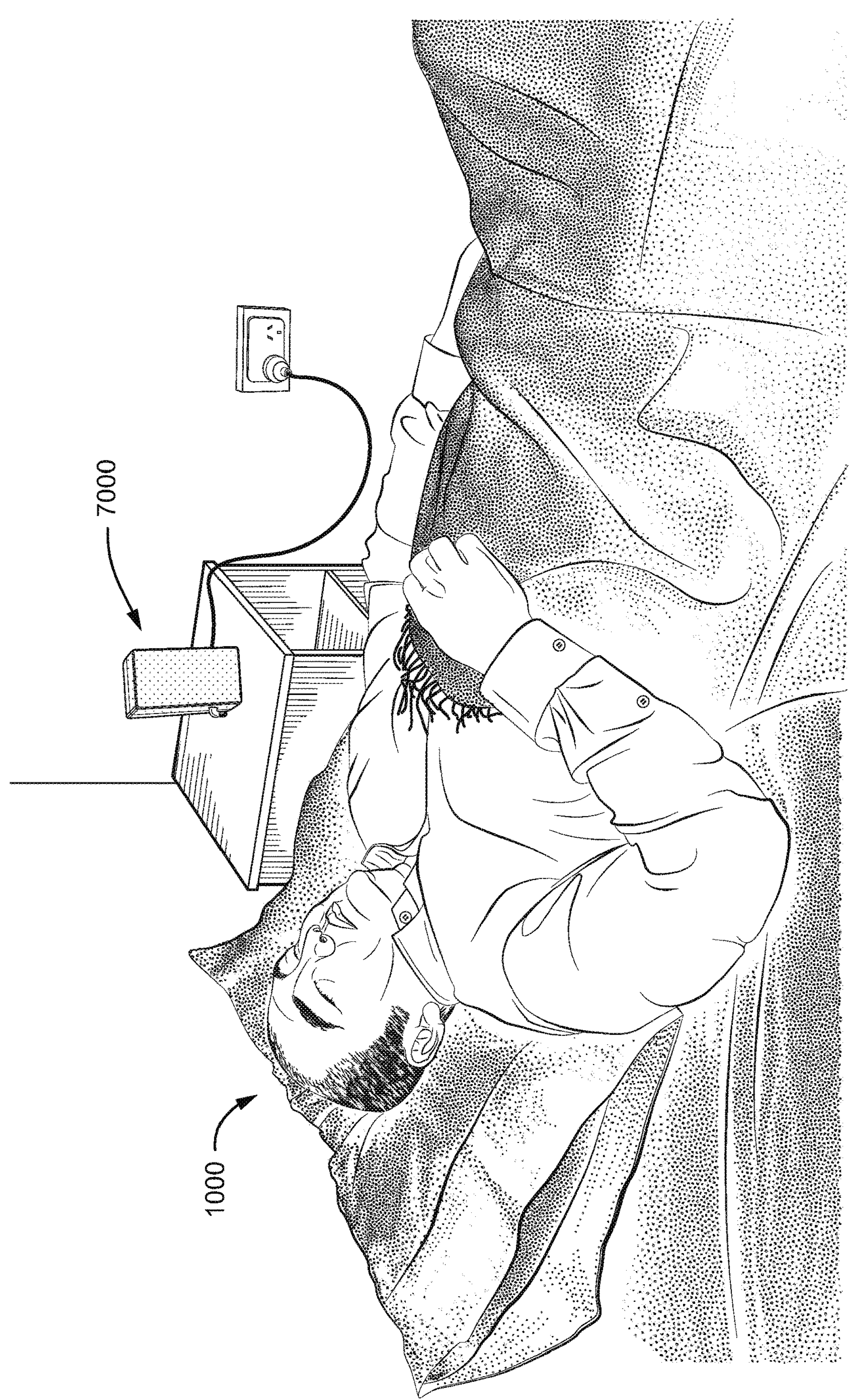

FIG. 7B shows a monitoring apparatus for monitoring the condition of a patient. The patient is sleeping in a supine sleeping position.

3.8 Data Transmission

Figure 8:
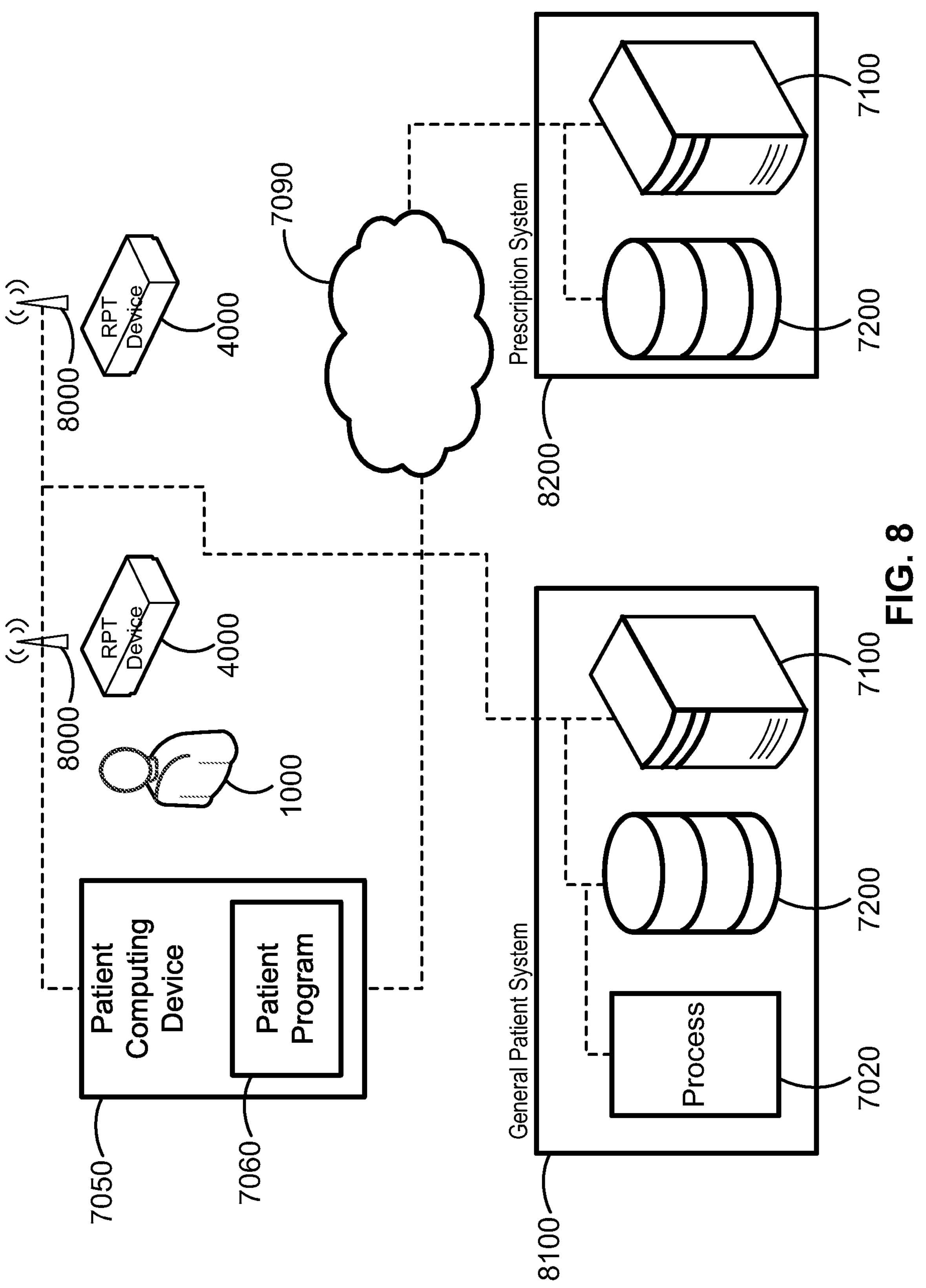

FIG. 8 shows a block diagram of a system for storing and updating prescription therapy settings for respiratory therapy devices.

3.9 Transferring Therapy Settings

Figure 9:
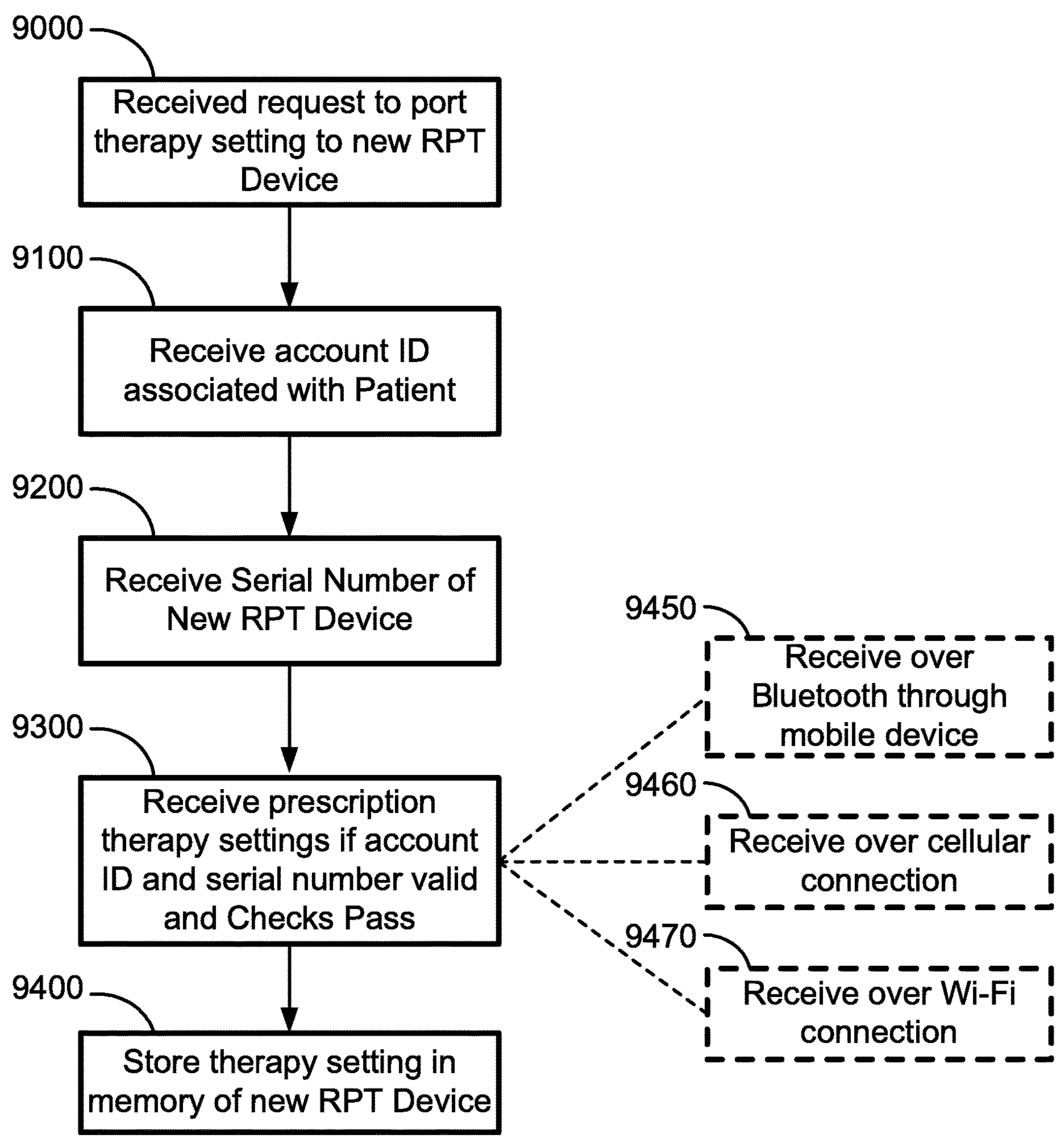

FIG. 9 shows a flow chart of an example of a method for storing prescription therapy settings on a respiratory therapy device.

Figure 10:
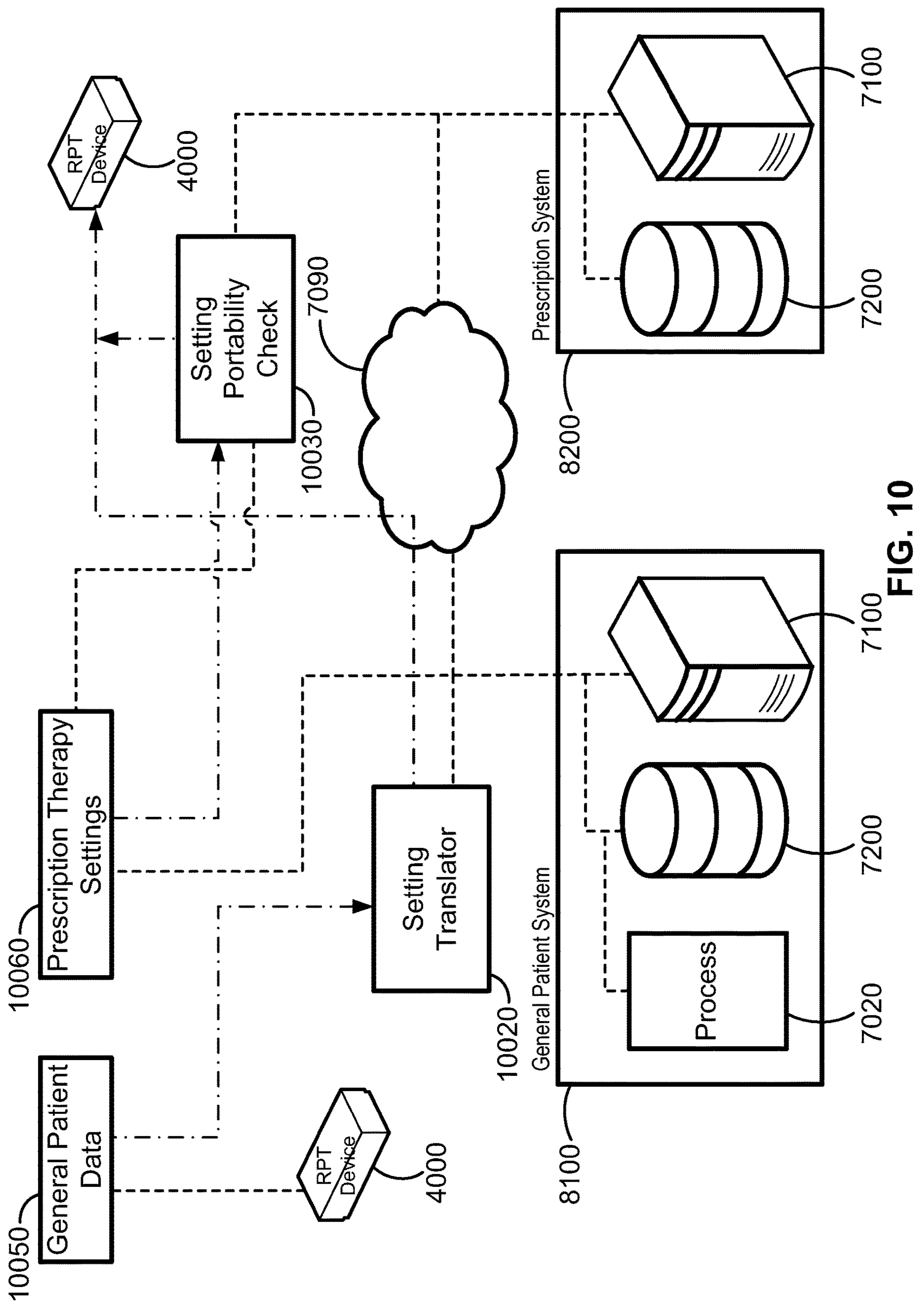

FIG. 10 shows a block diagram of a system for storing and updating prescription therapy settings for respiratory therapy device.

Figure 11:
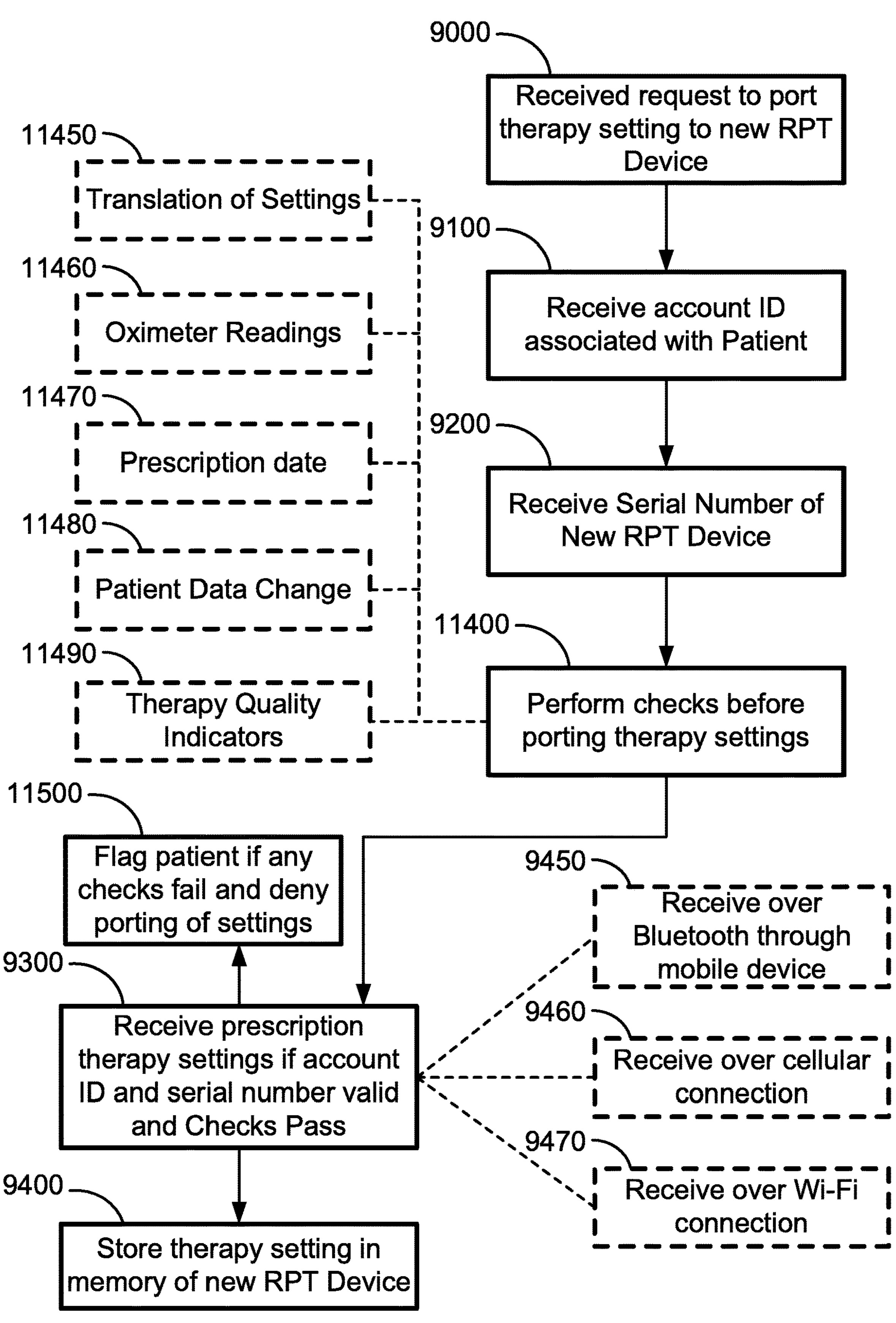

FIG. 11 shows a flow chart of an example of a method for storing and updating prescription therapy settings on a respiratory therapy device.

4 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

4.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

4.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000 or 3800.

4.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

An unsealed patient interface 3800, in the form of a nasal cannula, includes nasal prongs 3810*a*, 3810*b* which can deliver air to respective nares of the patient 1000. Such nasal prongs do not generally form a seal with the inner or outer skin surface of the flares. The air to the nasal prongs may be delivered by one or more air supply lumens 3820*a*, 3820*b* that are coupled with the nasal cannula 3800. The lumens 3820*a*, 3820*b* lead from the nasal cannula 3800 lead to an RT device that generates the flow of air at high flow rates. The "vent" at the unsealed patient interface 3800, through which excess airflow escapes to ambient, is the passage between the end of the prongs 3810*a* and 3810*b* of the cannula 3800 via the patient's nares to atmosphere.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 $cmH_2O$ with respect to ambient.

The patient interface 3000 in accordance with one form of the present technology is constructed and arranged to be able to provide a supply of air at a positive pressure of at least 10 $cmH_2O$ with respect to ambient.

The patient interface 3000 in accordance with one form of the present technology is constructed and arranged to be able to provide a supply of air at a positive pressure of at least 20 $cmH_2O$ with respect to ambient.

4.4 RPT Device

An RPT device 4000 in accordance with one aspect of the present technology comprises mechanical, pneumatic, and/or electrical components and is configured to execute one or more algorithms 4300, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 $cmH_2O$, or at least 10 $cmH_2O$, or at least 20 $cmH_2O$.

4.4.1 RPT Device Electrical Components

4.4.1.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

4.4.1.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

4.4.1.3 Central Controller

In one form of the present technology, the central controller 4230 is one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, one or more input devices 4220, and the humidifier 5000.

The central controller 4230 may be configured to provide output signal(s) to one or more of an output device 4290, a therapy device controller 4240, a data communication interface 4280, and the humidifier 5000.

In some forms of the present technology, the central controller 4230 is configured to implement the one or more methodologies described herein, such as the one or more algorithms 4300 expressed as computer programs stored in a non-transitory computer readable storage medium, such as memory 4260. In some forms of the present technology, the central controller 4230 may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

4.4.1.4 Clock

The RPT device 4000 may include a clock 4232 that is connected to the central controller 4230.

4.4.1.5 Therapy Device Controller

In one form of the present technology, therapy device controller 4240 is a therapy control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

4.4.1.6 Protection Circuits

The one or more protection circuits 4250 in accordance with the present technology may comprise an electrical protection circuit, a temperature and/or pressure safety circuit.

4.4.1.7 Memory

In accordance with one form of the present technology the RPT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

4.4.1.8 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile phone, tablet or remote control.

4.4.1.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

4.4.1.9.1 Display Driver

A display driver 4292 receives as an input the characters, symbols, or images intended for display on the display 4294, and converts them to commands that cause the display 4294 to display those characters, symbols, or images.

4.4.1.9.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

4.4.2 RPT Device Algorithms

As mentioned above, in some forms of the present technology, the central controller 4230 may be configured to implement one or more algorithms 4300 expressed as computer programs stored in a non-transitory computer readable storage medium, such as memory 4260. The algorithms 4300 are generally grouped into groups referred to as modules.

4.4.2.1 Pre-Processing Module

A pre-processing module 4310 in accordance with one form of the present technology receives as an input a signal from a transducer 4270, for example a flow rate sensor 4274 or pressure sensor 4272, and performs one or more process steps to calculate one or more output values that will be used as an input to another module, for example a therapy engine module 4320.

In one form of the present technology, the output values include the interface pressure Pm, the respiratory flow rate Qr, and the leak flow rate Ql.

In various forms of the present technology, the pre-processing module 4310 comprises one or more of the following algorithms: interface pressure estimation 4312, vent flow rate estimation 4314, leak flow rate estimation 4316, and respiratory flow rate estimation 4318.

4.4.2.1.1 Interface Pressure Estimation

In one form of the present technology, an interface pressure estimation algorithm 4312 receives as inputs a signal from the pressure sensor 4272 indicative of the pressure in the pneumatic path proximal to an outlet of the pneumatic block (the device pressure Pd) and a signal from the flow rate sensor 4274 representative of the flow rate of the airflow leaving the RPT device 4000 (the device flow rate Qd). The device flow rate Qd, absent any supplementary gas 4180, may be used as the total flow rate Qt. The interface pressure algorithm 4312 estimates the pressure drop ΔP through the air circuit 4170. The dependence of the pressure drop ΔP on the total flow rate Qt may be modelled for the particular air circuit 4170 by a pressure drop characteristic ΔP(Q). The interface pressure estimation algorithm, 4312 then provides as an output an estimated pressure, Pm, in the patient interface 3000 or 3800. The pressure, Pm, in the patient interface 3000 or 3800 may be estimated as the device pressure Pd minus the air circuit pressure drop ΔP.

4.4.2.1.2 Vent Flow Rate Estimation

In one form of the present technology, a vent flow rate estimation algorithm 4314 receives as an input an estimated pressure, Pm, in the patient interface 3000 or 3800 from the interface pressure estimation algorithm 4312 and estimates a vent flow rate of air, Qv, from a vent 3400 in a patient interface 3000 or 3800. The dependence of the vent flow rate Qv on the interface pressure Pm for the particular vent 3400 in use may be modelled by a vent characteristic Qv(Pm)

4.4.2.1.3 Leak Flow Rate Estimation

In one form of the present technology, a leak flow rate estimation algorithm 4316 receives as an input a total flow rate, Qt, and a vent flow rate Qv, and provides as an output an estimate of the leak flow rate Ql. In one form, the leak flow rate estimation algorithm estimates the leak flow rate Ql by calculating an average of the difference between total flow rate Qt and vent flow rate Qv over a period sufficiently long to include several breathing cycles, e.g. about 10 seconds.

In one form, the leak flow rate estimation algorithm 4316 receives as an input a total flow rate Qt, a vent flow rate Qv, and an estimated pressure, Pm, in the patient interface 3000 or 3800, and provides as an output a leak flow rate Ql, by calculating a leak conductance, and determining a leak flow rate Ql to be a function of leak conductance and pressure, Pm. Leak conductance is calculated as the quotient of low pass filtered non-vent flow rate equal to the difference between total flow rate Qt and vent flow rate Qv, and low pass filtered square root of pressure Pm, where the low pass filter time constant has a value sufficiently long to include several breathing cycles, e.g. about 10 seconds. The leak flow rate Ql may be estimated as the product of leak conductance and a function of pressure, Pm.

4.4.2.1.4 Respiratory Flow Rate Estimation

In one form of the present technology, a respiratory flow rate estimation algorithm 4318 receives as an input a total flow rate, Qt, a vent flow rate, Qv, and a leak flow rate, Ql, and estimates a respiratory flow rate of air, Qr, to the patient, by subtracting the vent flow rate Qv and the leak flow rate Ql from the total flow rate Qt.

4.4.2.2 Therapy Engine Module

In one form of the present technology, a therapy engine module 4320 receives as inputs one or more of a pressure, Pm, in a patient interface 3000 or 3800, and a respiratory flow rate of air to a patient, Qr, and provides as an output one or more therapy parameters.

In one form of the present technology, a therapy parameter is a treatment pressure Pt.

In one form of the present technology, therapy parameters are one or more of an amplitude of a pressure variation, a base pressure, and a target ventilation.

In various forms, the therapy engine module 4320 comprises one or more of the following algorithms: phase determination 4321, waveform determination 4322, ventilation determination 4323, inspiratory flow limitation determination 4324, apnea/hypopnea determination 4325, snore determination 4326, airway patency determination 4327, target ventilation determination 4328, and therapy parameter determination 4329.

4.4.2.2.1 Phase Determination

In one form of the present technology, the RPT device 4000 does not determine phase.

In one form of the present technology, a phase determination algorithm 4321 receives as an input a signal indicative of respiratory flow rate, Qr, and provides as an output a phase Φ of a current breathing cycle of a patient 1000.

In some forms, known as discrete phase determination, the phase output Φ is a discrete variable. One implementation of discrete phase determination provides a bi-valued phase output Φ with values of either inhalation or exhalation, for example represented as values of 0 and 0.5 revolutions respectively, upon detecting the start of spontaneous inhalation and exhalation respectively. RPT devices 4000 that "trigger" and "cycle" effectively perform discrete phase determination, since the trigger and cycle points are the instants at which the phase changes from exhalation to inhalation and from inhalation to exhalation, respectively. In one implementation of bi-valued phase determination, the phase output Φ is determined to have a discrete value of 0 (thereby "triggering" the RPT device 4000) when the respiratory flow rate Qr has a value that exceeds a positive threshold, and a discrete value of 0.5 revolutions (thereby "cycling" the RPT device 4000) when a respiratory flow rate Qr has a value that is more negative than a negative threshold. The inhalation time Ti and the exhalation time Te may be estimated as typical values over many respiratory cycles of the time spent with phase Φ equal to 0 (indicating inspiration) and 0.5 (indicating expiration) respectively.

Another implementation of discrete phase determination provides a tri-valued phase output Φ with a value of one of inhalation, mid-inspiratory pause, and exhalation.

In other forms, known as continuous phase determination, the phase output Φ is a continuous variable, for example varying from 0 to 1 revolutions, or 0 to 2π radians. RPT devices 4000 that perform continuous phase determination may trigger and cycle when the continuous phase reaches 0 and 0.5 revolutions, respectively. In one implementation of continuous phase determination, a continuous value of phase Φ is determined using a fuzzy logic analysis of the respiratory flow rate Qr. A continuous value of phase determined in this implementation is often referred to as "fuzzy phase". In one implementation of a fuzzy phase determination algorithm 4321, the following rules are applied to the respiratory flow rate Qr:

1. If the respiratory flow rate is zero and increasing fast then the phase is 0 revolutions.
2. If the respiratory flow rate is large positive and steady then the phase is 0.25 revolutions.
3. If the respiratory flow rate is zero and falling fast, then the phase is 0.5 revolutions.
4. If the respiratory flow rate is large negative and steady then the phase is 0.75 revolutions.

5. If the respiratory flow rate is zero and steady and the 5-second low-pass filtered absolute value of the respiratory flow rate is large then the phase is 0.9 revolutions.
6. If the respiratory flow rate is positive and the phase is expiratory, then the phase is 0 revolutions.
7. If the respiratory flow rate is negative and the phase is inspiratory, then the phase is 0.5 revolutions.
8. If the 5-second low-pass filtered absolute value of the respiratory flow rate is large, the phase is increasing at a steady rate equal to the patient's breathing rate, low-pass filtered with a time constant of 20 seconds.

The output of each rule may be represented as a vector whose phase is the result of the rule and whose magnitude is the fuzzy extent to which the rule is true. The fuzzy extent to which the respiratory flow rate is "large", "steady", etc. is determined with suitable membership functions. The results of the rules, represented as vectors, are then combined by some function such as taking the centroid. In such a combination, the rules may be equally weighted, or differently weighted.

In another implementation of continuous phase determination, the phase Φ is first discretely estimated from the respiratory flow rate Qr as described above, as are the inhalation time Ti and the exhalation time Te. The continuous phase Φ at any instant may be determined as the half the proportion of the inhalation time Ti that has elapsed since the previous trigger instant, or 0.5 revolutions plus half the proportion of the exhalation time Te that has elapsed since the previous cycle instant (whichever instant was more recent).

4.4.2.2.2 Waveform Determination

In one form of the present technology, the therapy parameter determination algorithm 4329 provides an approximately constant treatment pressure throughout a respiratory cycle of a patient.

In other forms of the present technology, the therapy control module 4330 controls the pressure generator 4140 to provide a treatment pressure Pt that varies as a function of phase Φ of a respiratory cycle of a patient according to a waveform template Π(Φ).

In one form of the present technology, a waveform determination algorithm 4322 provides a waveform template Π(Φ) with values in the range [0, 1] on the domain of phase values Φ provided by the phase determination algorithm 4321 to be used by the therapy parameter determination algorithm 4329.

In one form, suitable for either discrete or continuously-valued phase, the waveform template Π(Φ) is a square-wave template, having a value of 1 for values of phase up to and including 0.5 revolutions, and a value of 0 for values of phase above 0.5 revolutions. In one form, suitable for continuously-valued phase, the waveform template Π(Φ) comprises two smoothly curved portions, namely a smoothly curved (e.g. raised cosine) rise from 0 to 1 for values of phase up to 0.5 revolutions, and a smoothly curved (e.g. exponential) decay from 1 to 0 for values of phase above 0.5 revolutions. In one form, suitable for continuously-valued phase, the waveform template Π(Φ) is based on a square wave, but with a smooth rise from 0 to 1 for values of phase up to a "rise time" that is less than 0.5 revolutions, and a smooth fall from 1 to 0 for values of phase within a "fall time" after 0.5 revolutions, with a "fall time" that is less than 0.5 revolutions.

In some forms of the present technology, the waveform determination algorithm 4322 selects a waveform template Π(Φ) from a library of waveform templates, dependent on a setting of the RPT device. Each waveform template Π(Φ) in the library may be provided as a lookup table of values Π against phase values Φ. In other forms, the waveform determination algorithm 4322 computes a waveform template Π(Φ) "on the fly" using a predetermined functional form, possibly parametrised by one or more parameters (e.g. time constant of an exponentially curved portion). The parameters of the functional form may be predetermined or dependent on a current state of the patient 1000.

In some forms of the present technology, suitable for discrete bi-valued phase of either inhalation (Φ=0 revolutions) or exhalation (Φ=0.5 revolutions), the waveform determination algorithm 4322 computes a waveform template Π "on the fly" as a function of both discrete phase Φ and time t measured since the most recent trigger instant. In one such form, the waveform determination algorithm 4322 computes the waveform template Π(Φ, t) in two portions (inspiratory and expiratory) as follows:

$$\Pi(\Phi, t) = \begin{cases} \Pi_i(t), & \Phi = 0 \\ \Pi_e(t - T_i), & \Phi = 0.5 \end{cases}$$

where $\Pi_i(t)$ and $\Pi_e(t)$ are inspiratory and expiratory portions of the waveform template Π(Φ, t). In one such form, the inspiratory portion $\Pi_i(t)$ of the waveform template is a smooth rise from 0 to 1 parametrised by a rise time, and the expiratory portion $\Pi_e(t)$ of the waveform template is a smooth fall from 1 to 0 parametrised by a fall time.

4.4.2.2.3 Ventilation Determination

In one form of the present technology, a ventilation determination algorithm 4323 receives an input a respiratory flow rate Qr, and determines a measure indicative of current patient ventilation, Vent.

In some implementations, the ventilation determination algorithm 4323 determines a measure of ventilation Vent that is an estimate of actual patient ventilation. One such implementation is to take half the absolute value of respiratory flow rate, Qr, optionally filtered by low-pass filter such as a second order Bessel low-pass filter with a corner frequency of 0.11 Hz.

In other implementations, the ventilation determination algorithm 4323 determines a measure of ventilation Vent that is broadly proportional to actual patient ventilation. One such implementation estimates peak respiratory flow rate Qpeak over the inspiratory portion of the cycle. This and many other procedures involving sampling the respiratory flow rate Qr produce measures which are broadly proportional to ventilation, provided the flow rate waveform shape does not vary very much (here, the shape of two breaths is taken to be similar when the flow rate waveforms of the breaths normalised in time and amplitude are similar). Some simple examples include the median positive respiratory flow rate, the median of the absolute value of respiratory flow rate, and the standard deviation of flow rate. Arbitrary linear combinations of arbitrary order statistics of the absolute value of respiratory flow rate using positive coefficients, and even some using both positive and negative coefficients, are approximately proportional to ventilation. Another example is the mean of the respiratory flow rate in the middle K proportion (by time) of the inspiratory portion, where $0<K<1$. There is an arbitrarily large number of measures that are exactly proportional to ventilation if the flow rate shape is constant.

4.4.2.2.4 Determination of Inspiratory Flow limitation

In one form of the present technology, the central controller 4230 executes an inspiratory flow limitation determination algorithm 4324 for the determination of the extent of inspiratory flow limitation.

In one form, the inspiratory flow limitation determination algorithm 4324 receives as an input a respiratory flow rate signal Qr and provides as an output a metric of the extent to which the inspiratory portion of the breath exhibits inspiratory flow limitation.

In one form of the present technology, the inspiratory portion of each breath is identified by a zero-crossing detector. A number of evenly spaced points (for example, sixty-five), representing points in time, are interpolated by an interpolator along the inspiratory flow rate-time curve for each breath. The curve described by the points is then scaled by a scalar to have unity length (duration/period) and unity area to remove the effects of changing breathing rate and depth. The scaled breaths are then compared in a comparator with a pre-stored template representing a normal unobstructed breath, similar to the inspiratory portion of the breath shown in FIG. 6A. Breaths deviating by more than a specified threshold (typically 1 scaled unit) at any time during the inspiration from this template, such as those due to coughs, sighs, swallows and hiccups, as determined by a test element, are rejected. For non-rejected data, a moving average of the first such scaled point is calculated by the central controller 4230 for the preceding several inspiratory events. This is repeated over the same inspiratory events for the second such point, and so on. Thus, for example, sixty five scaled data points are generated by the central controller 4230, and represent a moving average of the preceding several inspiratory events, e.g., three events. The moving average of continuously updated values of the (e.g., sixty five) points are hereinafter called the "scaled flow rate", designated as Qs(t). Alternatively, a single inspiratory event can be utilised rather than a moving average.

From the scaled flow rate, two shape factors relating to the determination of partial obstruction may be calculated.

Shape factor 1 is the ratio of the mean of the middle (e.g. thirty-two) scaled flow rate points to the mean overall (e.g. sixty-five) scaled flow rate points. Where this ratio is in excess of unity, the breath will be taken to be normal. Where the ratio is unity or less, the breath will be taken to be obstructed. A ratio of about 1.17 is taken as a threshold between partially obstructed and unobstructed breathing, and equates to a degree of obstruction that would permit maintenance of adequate oxygenation in a typical patient.

Shape factor 2 is calculated as the RMS deviation from unit scaled flow rate, taken over the middle (e.g. thirty-two) points. An RMS deviation of about 0.2 units is taken to be normal. An RMS deviation of zero is taken to be a totally flow-limited breath. The closer the RMS deviation to zero, the breath will be taken to be more flow limited.

Shape factors 1 and 2 may be used as alternatives, or in combination. In other forms of the present technology, the number of sampled points, breaths and middle points may differ from those described above. Furthermore, the threshold values can be other than those described.

4.4.2.2.5 Determination of Apneas and Hypopneas

In one form of the present technology, the central controller 4230 executes an apnea/hypopnea determination algorithm 4325 for the determination of the presence of apneas and/or hypopneas.

In one form, the apnea/hypopnea determination algorithm 4325 receives as an input a respiratory flow rate signal Qr and provides as an output a flag that indicates that an apnea or a hypopnea has been detected.

In one form, an apnea will be said to have been detected when a function of respiratory flow rate Qr falls below a flow rate threshold for a predetermined period of time. The function may determine a peak flow rate, a relatively short-term mean flow rate, or a flow rate intermediate of relatively short-term mean and peak flow rate, for example an RMS flow rate. The flow rate threshold may be a relatively long-term measure of flow rate.

In one form, a hypopnea will be said to have been detected when a function of respiratory flow rate Qr falls below a second flow rate threshold for a predetermined period of time. The function may determine a peak flow, a relatively short-term mean flow rate, or a flow rate intermediate of relatively short-term mean and peak flow rate, for example an RMS flow rate. The second flow rate threshold may be a relatively long-term measure of flow rate. The second flow rate threshold is greater than the flow rate threshold used to detect apneas.

4.4.2.2.6 Determination of Snore

In one form of the present technology, the central controller 4230 executes one or more snore determination algorithms 4326 for the determination of the extent of snore.

In one form, the snore determination algorithm 4326 receives as an input a respiratory flow rate signal Qr and provides as an output a metric of the extent to which snoring is present.

The snore determination algorithm 4326 may comprise the step of determining the intensity of the flow rate signal in the range of 30-300 Hz. Further, the snore determination algorithm 4326 may comprise a step of filtering the respiratory flow rate signal Qr to reduce background noise, e.g., the sound of airflow in the system from the blower.

4.4.2.2.7 Determination of Airway Patency

In one form of the present technology, the central controller 4230 executes one or more airway patency determination algorithms 4327 for the determination of the extent of airway patency.

In one form, the airway patency determination algorithm 4327 receives as an input a respiratory flow rate signal Qr, and determines the power of the signal in the frequency range of about 0.75 Hz and about 3 Hz. The presence of a peak in this frequency range is taken to indicate an open airway. The absence of a peak is taken to be an indication of a closed airway.

In one form, the frequency range within which the peak is sought is the frequency of a small forced oscillation in the treatment pressure Pt. In one implementation, the forced oscillation is of frequency 2 Hz with amplitude about 1 $cmH_2O$.

In one form, airway patency determination algorithm 4327 receives as an input a respiratory flow rate signal Qr, and determines the presence or absence of a cardiogenic signal. The absence of a cardiogenic signal is taken to be an indication of a closed airway.

4.4.2.2.8 Determination of Target Ventilation

In one form of the present technology, the central controller 4230 takes as input the measure of current ventilation, Vent, and executes one or more target ventilation determination algorithms 4328 for the determination of a target value Vtgt for the measure of ventilation.

In some forms of the present technology, there is no target ventilation determination algorithm 4328, and the target value Vtgt is predetermined, for example by hard-coding during configuration of the RPT device 4000 or by manual entry through the input device 4220.

In other forms of the present technology, such as adaptive servo-ventilation (ASV), the target ventilation determination algorithm 4328 computes a target value Vtgt from a value Vtyp indicative of the typical recent ventilation of the patient.

In some forms of adaptive servo-ventilation, the target ventilation Vtgt is computed as a high proportion of, but less than, the typical recent ventilation Vtyp. The high proportion in such forms may be in the range (80%, 100%), or (85%, 95%), or (87%, 92%).

In other forms of adaptive servo-ventilation, the target ventilation Vtgt is computed as a slightly greater than unity multiple of the typical recent ventilation Vtyp.

The typical recent ventilation Vtyp is the value around which the distribution of the measure of current ventilation Vent over multiple time instants over some predetermined timescale tends to cluster, that is, a measure of the central tendency of the measure of current ventilation over recent history. In one implementation of the target ventilation determination algorithm 4328, the recent history is of the order of several minutes, but in any case should be longer than the timescale of Cheyne-Stokes waxing and waning cycles. The target ventilation determination algorithm 4328 may use any of the variety of well-known measures of central tendency to determine the typical recent ventilation Vtyp from the measure of current ventilation, Vent. One such measure is the output of a low-pass filter on the measure of current ventilation Vent, with time constant equal to one hundred seconds.

4.4.2.2.9 Determination of Therapy Parameters

In some forms of the present technology, the central controller 4230 executes one or more therapy parameter determination algorithms 4329 for the determination of one or more therapy parameters using the values returned by one or more of the other algorithms in the therapy engine module 4320.

In one form of the present technology, the therapy parameter is an instantaneous treatment pressure Pt. In one implementation of this form, the therapy parameter determination algorithm 4329 determines the treatment pressure Pt using the equation $$Pt = A\prod(\Phi, t) + P_0 \qquad (1)$$

where:

A is the amplitude, $\Pi(\Phi, t)$ is the waveform template value (in the range 0 to 1) at the current value $\Phi$ of phase and t of time, and $P_0$ is a base pressure.

If the waveform determination algorithm 4322 provides the waveform template $\Pi(\Phi, t)$ as a lookup table of values $\Pi$ indexed by phase $\Phi$, the therapy parameter determination algorithm 4329 applies equation (1) by locating the nearest lookup table entry to the current value $\Phi$ of phase returned by the phase determination algorithm 4321, or by interpolation between the two entries straddling the current value $\Phi$ of phase.

The values of the amplitude A and the base pressure $P_0$ may be set by the therapy parameter determination algorithm 4329 depending on the chosen respiratory pressure therapy mode in the manner described below.

4.4.2.3 Therapy Control Module

The therapy control module 4330 in accordance with one aspect of the present technology receives as inputs the therapy parameters from the therapy parameter determination algorithm 4329 of the therapy engine module 4320, and controls the pressure generator 4140 to deliver a flow of air in accordance with the therapy parameters.

In one form of the present technology, the therapy parameter is a treatment pressure Pt, and the therapy control module 4330 controls the pressure generator 4140 to deliver a flow of air whose interface pressure Pm at the patient interface 3000 or 3800 is equal to the treatment pressure Pt.

4.4.2.4 Detection of Fault Conditions

In one form of the present technology, the central controller 4230 executes one or more methods 4340 for the detection of fault conditions. The fault conditions detected by the one or more methods 4340 may include at least one of the following:

- Power failure (no power, or insufficient power)
- Transducer fault detection
- Failure to detect the presence of a component
- Operating parameters outside recommended ranges (e.g. pressure, flow rate, temperature, $PaO_2$)
- Failure of a test alarm to generate a detectable alarm signal.

Upon detection of the fault condition, the corresponding algorithm 4340 signals the presence of the fault by one or more of the following:

- Initiation of an audible, visual &/or kinetic (e.g. vibrating) alarm
- Sending a message to an external device
- Logging of the incident 4.5 Air Circuit An air circuit 4170 in accordance with an aspect of the present technology is a conduit or a tube constructed and arranged to allow, in use, a flow of air to travel between two components such as RPT device 4000 and the patient interface 3000 or 3800.

4.6 Humidifier 4.6.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

4.6.2 Humidifier Components 4.6.2.1 Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base 5006 where heat may be provided to the humidifier reservoir 5110 primarily by conduction as shown in FIG. 5B.

4.6.2.2 Humidifier Controller

According to one arrangement of the present technology, a humidifier 5000 may comprise a humidifier controller 5250 as shown in FIG. 5C. In one form, the humidifier controller 5250 may be a part of the central controller 4230. In another form, the humidifier controller 5250 may be a separate controller, which may be in communication with the central controller 4230.

In one form, the humidifier controller 5250 may receive as inputs measures of properties (such as temperature, humidity, pressure and/or flow rate), for example of the flow of air, the water in the reservoir 5110 and/or the humidifier 5000. The humidifier controller 5250 may also be configured to execute or implement humidifier algorithms and/or deliver one or more output signals.

As shown in FIG. 5C, the humidifier controller 5250 may comprise one or more controllers, such as a central humidifier controller 5251, a heated air circuit controller 5254 configured to control the temperature of a heated air circuit 4171 and/or a heating element controller 5252 configured to control the temperature of a heating element 5240.

4.7 Breathing Waveforms

FIG. 6A shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time Ti 1.6 s, peak inspiratory flow rate Qpeak 0.4 L/s, exhalation time Te 2.4 s, peak expiratory flow rate Qpeak −0.5 L/s. The total duration of the breath, Ttot, is about 4 s. The person typically breathes at a rate of about 15 breaths per minute (BPM), with Ventilation Vent about 7.5 L/min. A typical duty cycle, the ratio of Ti to Ttot, is about 40%.

4.8 Screening, Diagnosis, Monitoring Systems 4.8.1 Polysomnography

FIG. 7A shows a patient 1000 undergoing polysomnography (PSG). A PSG system comprises a headbox 2000 which receives and records signals from the following sensors: an EOG electrode 2015; an EEG electrode 2020; an ECG electrode 2025; a submental EMG electrode 2030; a snore sensor 2035; a respiratory inductance plethysmogram (respiratory effort sensor) 2040 on a chest band; a respiratory inductance plethysmogram (respiratory effort sensor) 2045 on an abdominal band; an oro-nasal cannula 2050 with oral thermistor; a photoplethysmograph (pulse oximeter) 2055; and a body position sensor 2060. The electrical signals are referred to a ground electrode (ISOG) 2010 positioned in the centre of the forehead.

4.8.2 Non-Obtrusive Monitoring System

One example of a monitoring apparatus 7100 for monitoring the respiration of a sleeping patient 1000 is illustrated in FIG. 7B. The monitoring apparatus 7100 contains a contactless motion sensor generally directed toward the patient 1000. The motion sensor is configured to generate one or more signals representing bodily movement of the patient 1000, from which may be obtained a signal representing respiratory movement of the patient.

4.8.3 Respiratory Polygraphy

Respiratory polygraphy (RPG) is a term for a simplified form of PSG without the electrical signals (EOG, EEG, EMG), snore, or body position sensors. RPG comprises at least a thoracic movement signal from a respiratory inductance plethysmogram (movement sensor) on a chest band, e.g. the movement sensor 2040, a nasal pressure signal sensed via a nasal cannula, and an oxygen saturation signal from a pulse oximeter, e.g. the pulse oximeter 2055. The three RPG signals, or channels, are received by an RPG headbox, similar to the PSG headbox 2000.

In certain configurations, a nasal pressure signal is a satisfactory proxy for a nasal flow rate signal generated by a flow rate transducer in-line with a sealed nasal mask, in that the nasal pressure signal is comparable in shape to the nasal flow rate signal. The nasal flow rate in turn is equal to the respiratory flow rate if the patient's mouth is kept closed, i.e. in the absence of mouth leaks.

4.9 Respiratory Therapy Modes

Various respiratory therapy modes may be implemented by the RPT device 4000.

4.9.1 CPAP Therapy

In some implementations of respiratory pressure therapy, the central controller 4230 sets the treatment pressure Pt according to the treatment pressure equation (1) as part of the therapy parameter determination algorithm 4329. In one such implementation, the amplitude A is identically zero, so the treatment pressure Pt (which represents a target value to be achieved by the interface pressure Pm at the current instant of time) is identically equal to the base pressure $P_0$ throughout the respiratory cycle. Such implementations are generally grouped under the heading of CPAP therapy. In such implementations, there is no need for the therapy engine module 4320 to determine phase $\Phi$ or the waveform template $\Pi(\Phi)$.

In CPAP therapy, the base pressure $P_0$ may be a constant value that is hard-coded or manually entered to the RPT device 4000. Alternatively, the central controller 4230 may repeatedly compute the base pressure $P_0$ as a function of indices or measures of sleep disordered breathing returned by the respective algorithms in the therapy engine module 4320, such as one or more of flow limitation, apnea, hypopnea, patency, and snore. This alternative is sometimes referred to as APAP therapy.

Figure 1A:
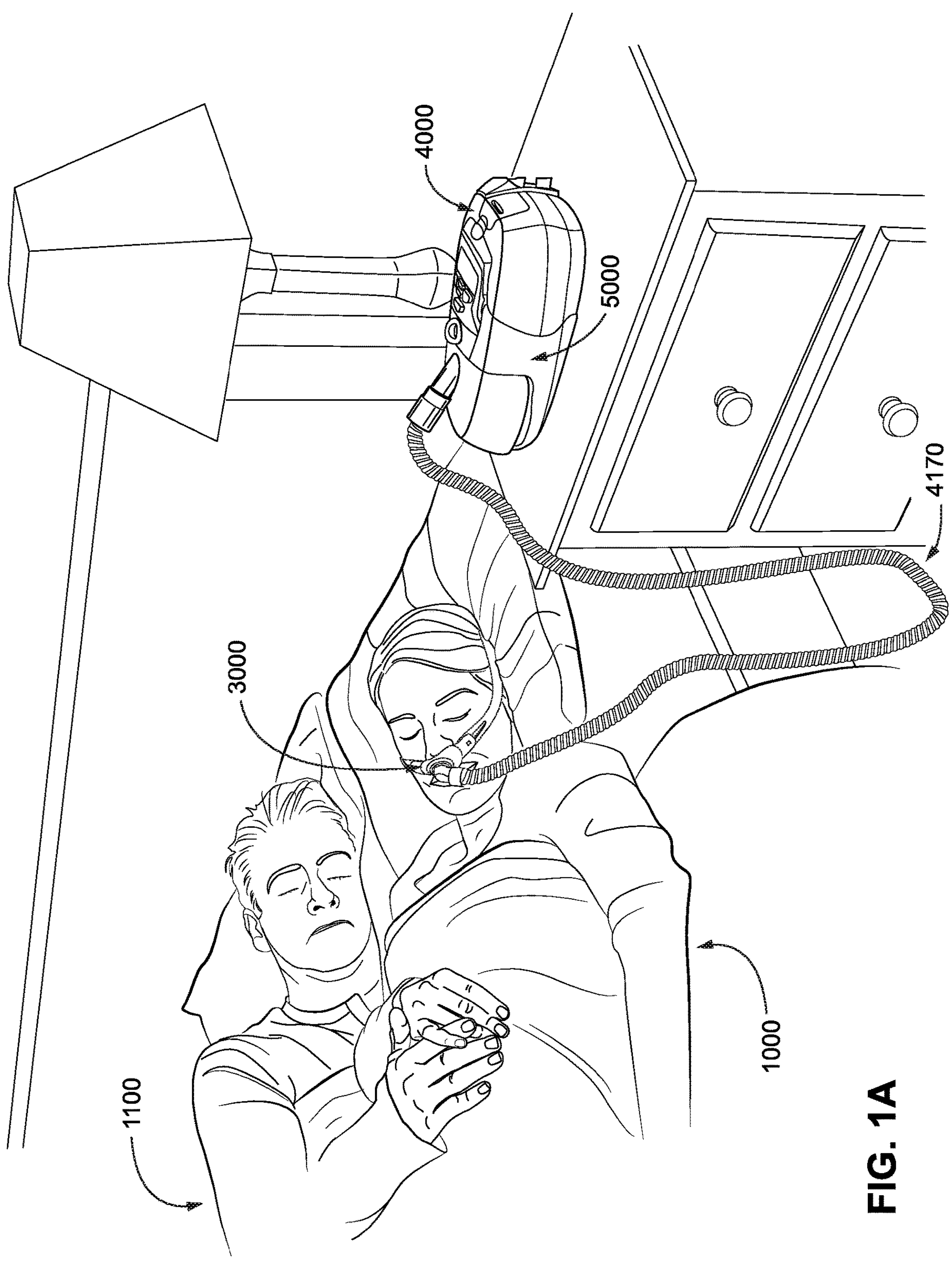
Figure 1B:
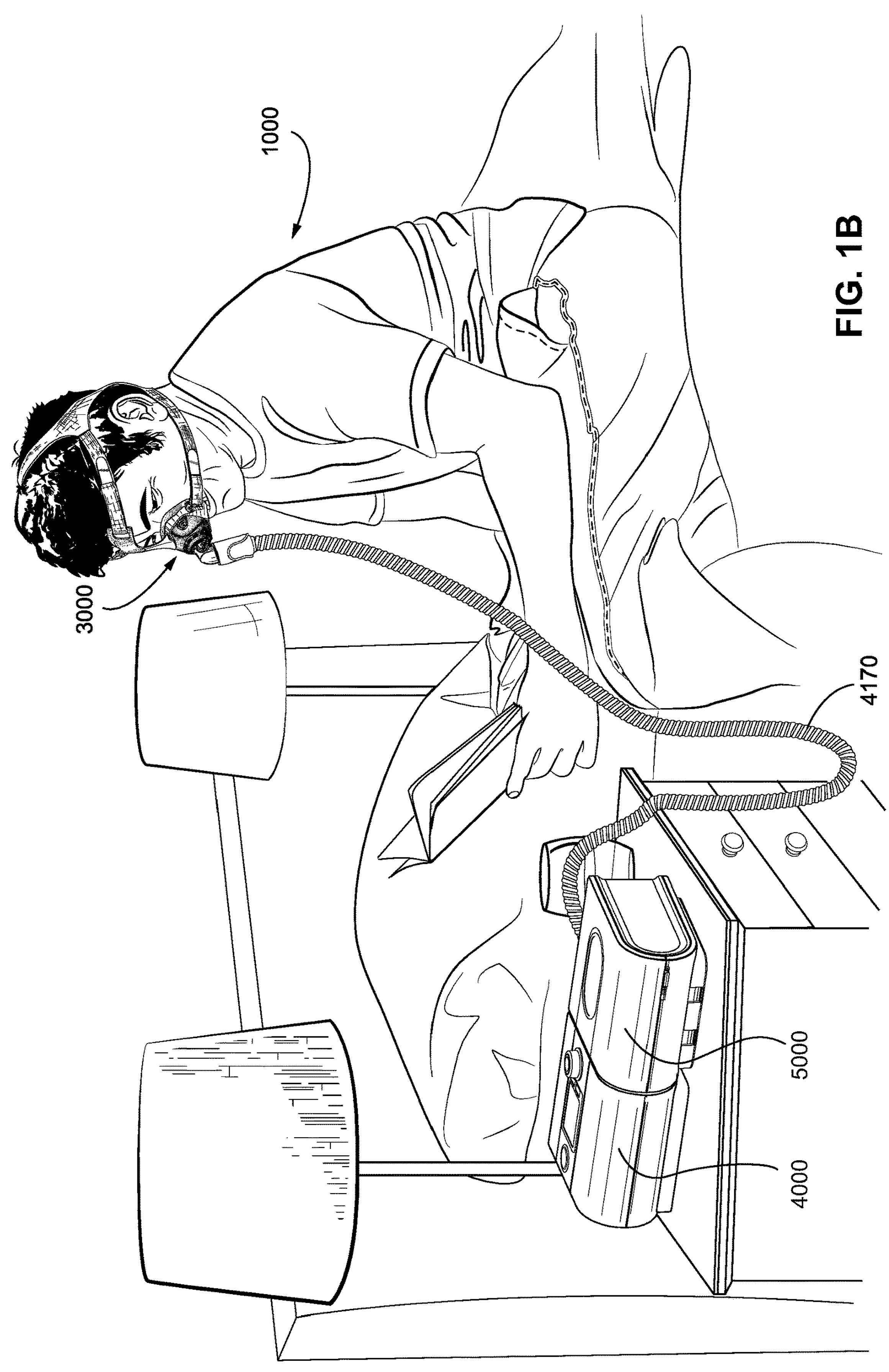
Figure 1C:
Figure 2A:
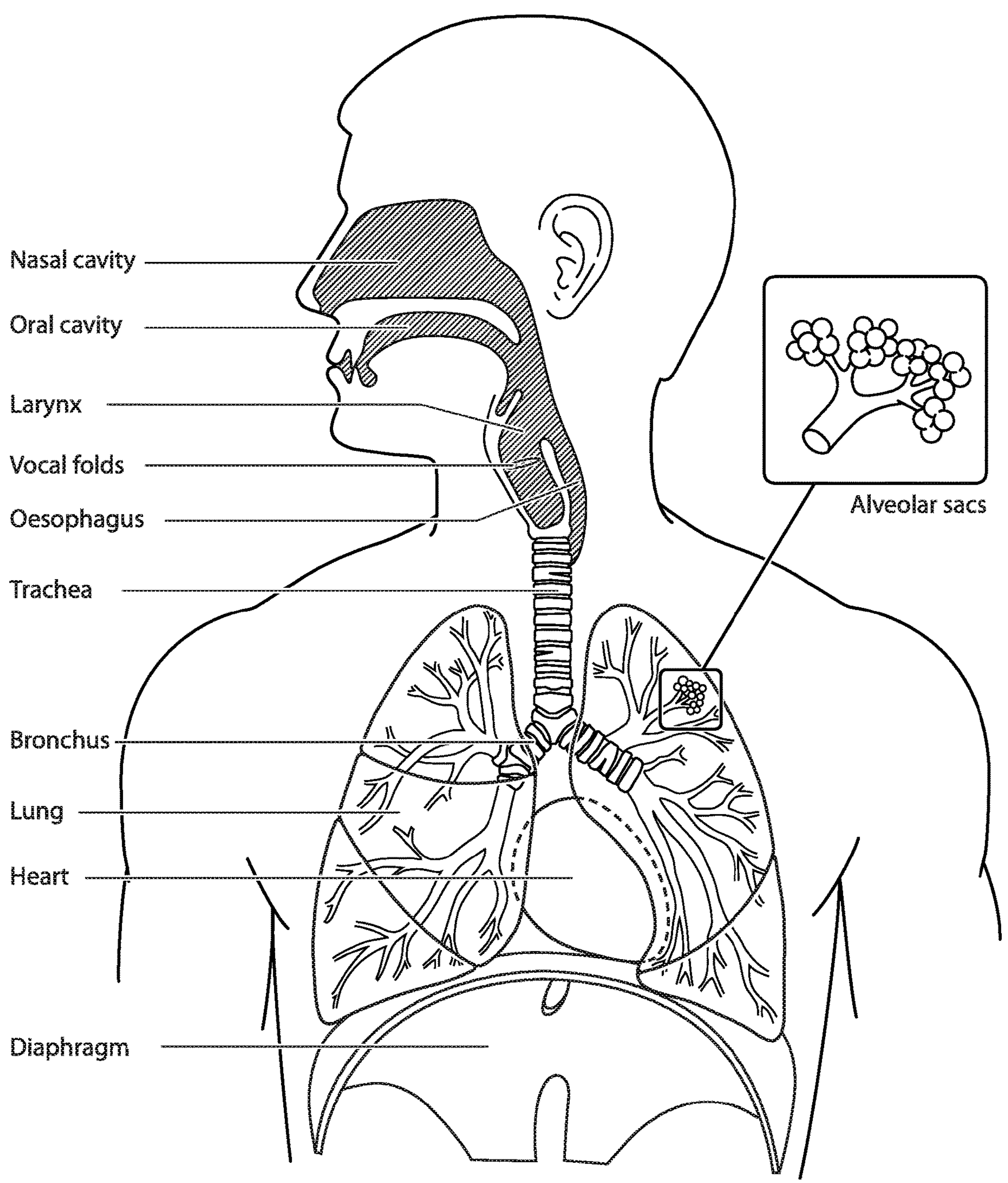
Figure 3A:
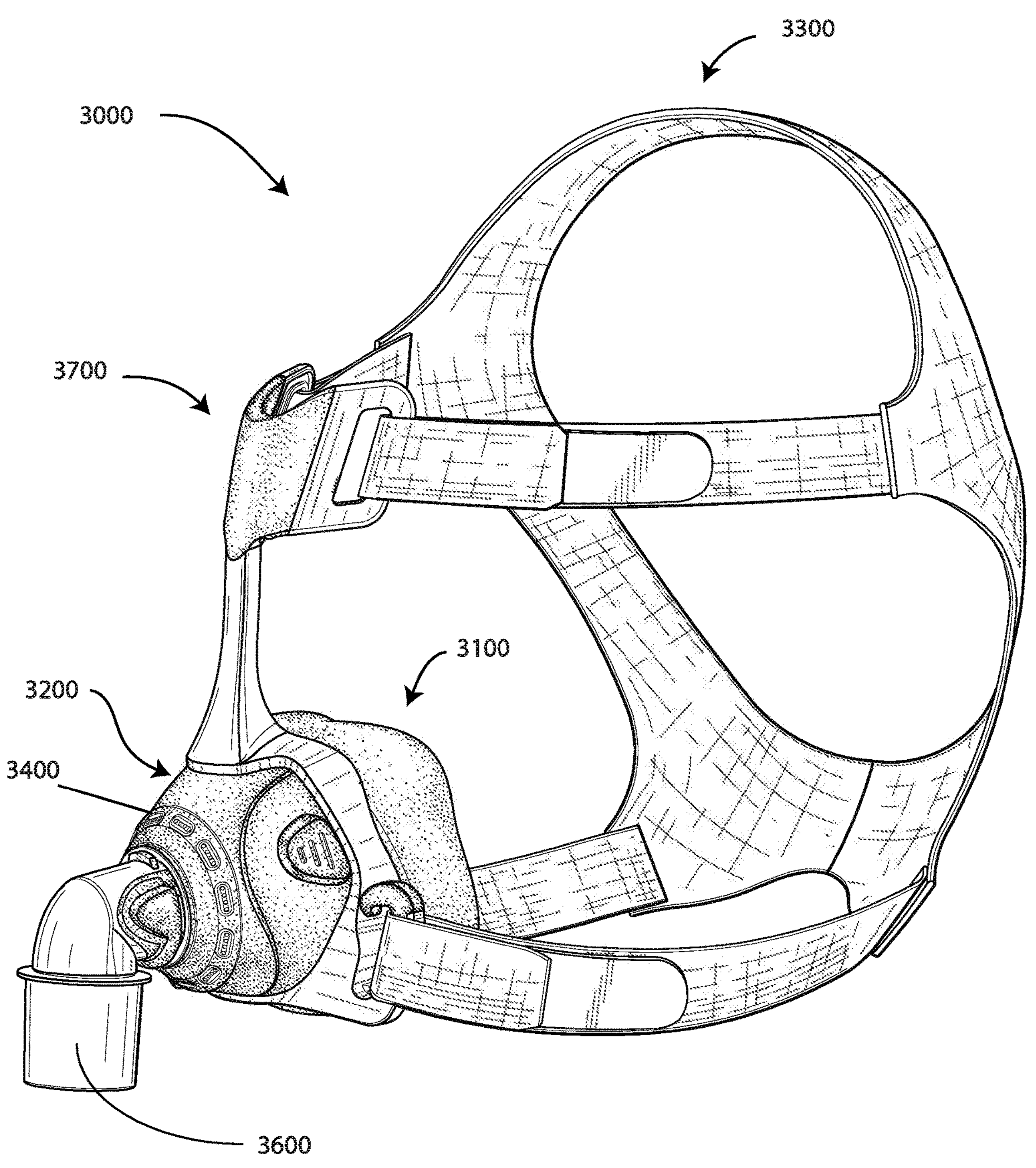
Figure 4A:
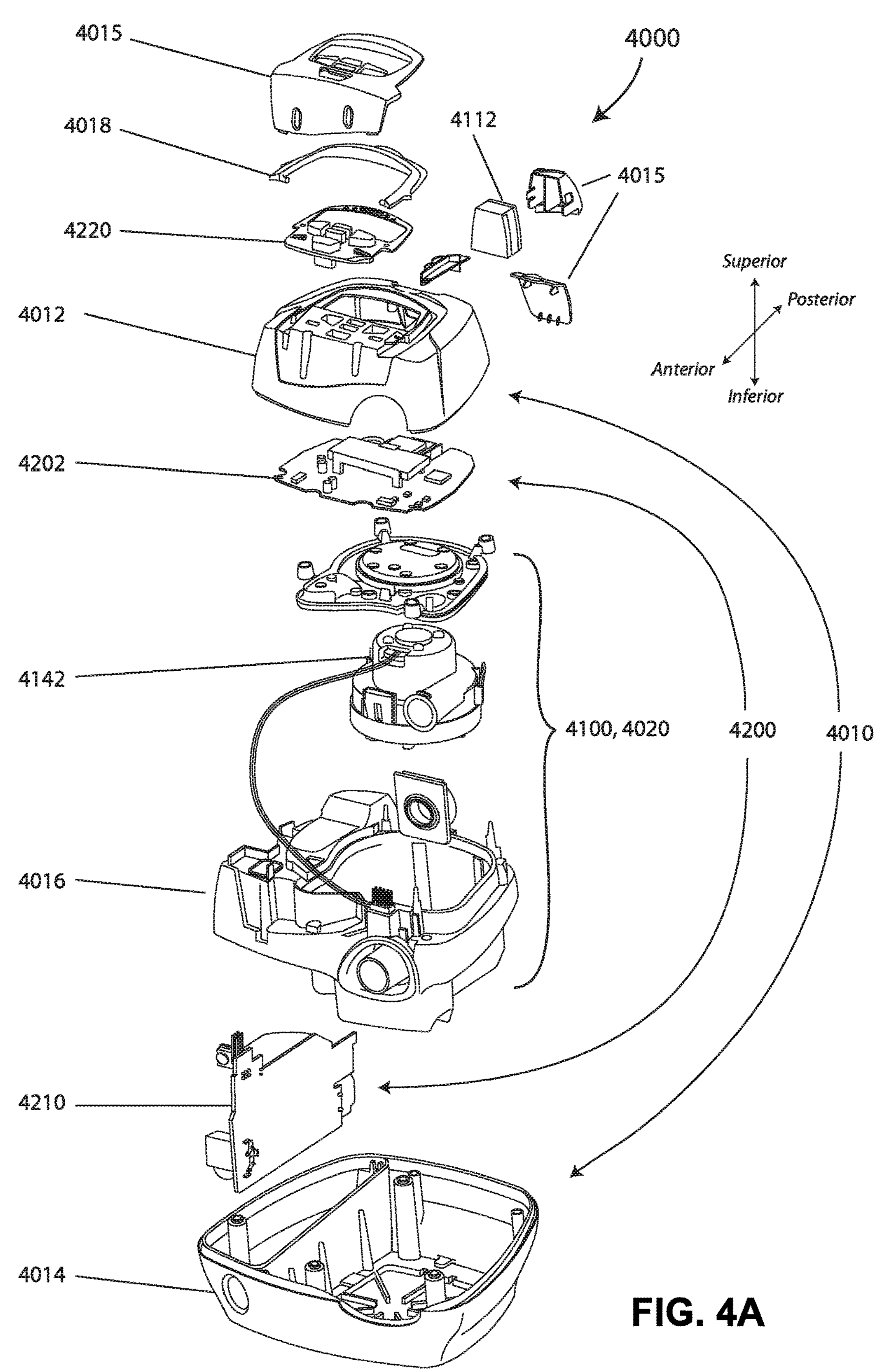
FIG. 4C is a schematic diagram of the electrical components of an RPT device in accordance with one form of the present technology.
FIG. 4D is a schematic diagram of the algorithms implemented in an RPT device in accordance with one form of the present technology.
FIG. 4E is a flow chart illustrating a method carried out by the therapy engine module of FIG. 4D in accordance with one form of the present technology.
Figure 4B:
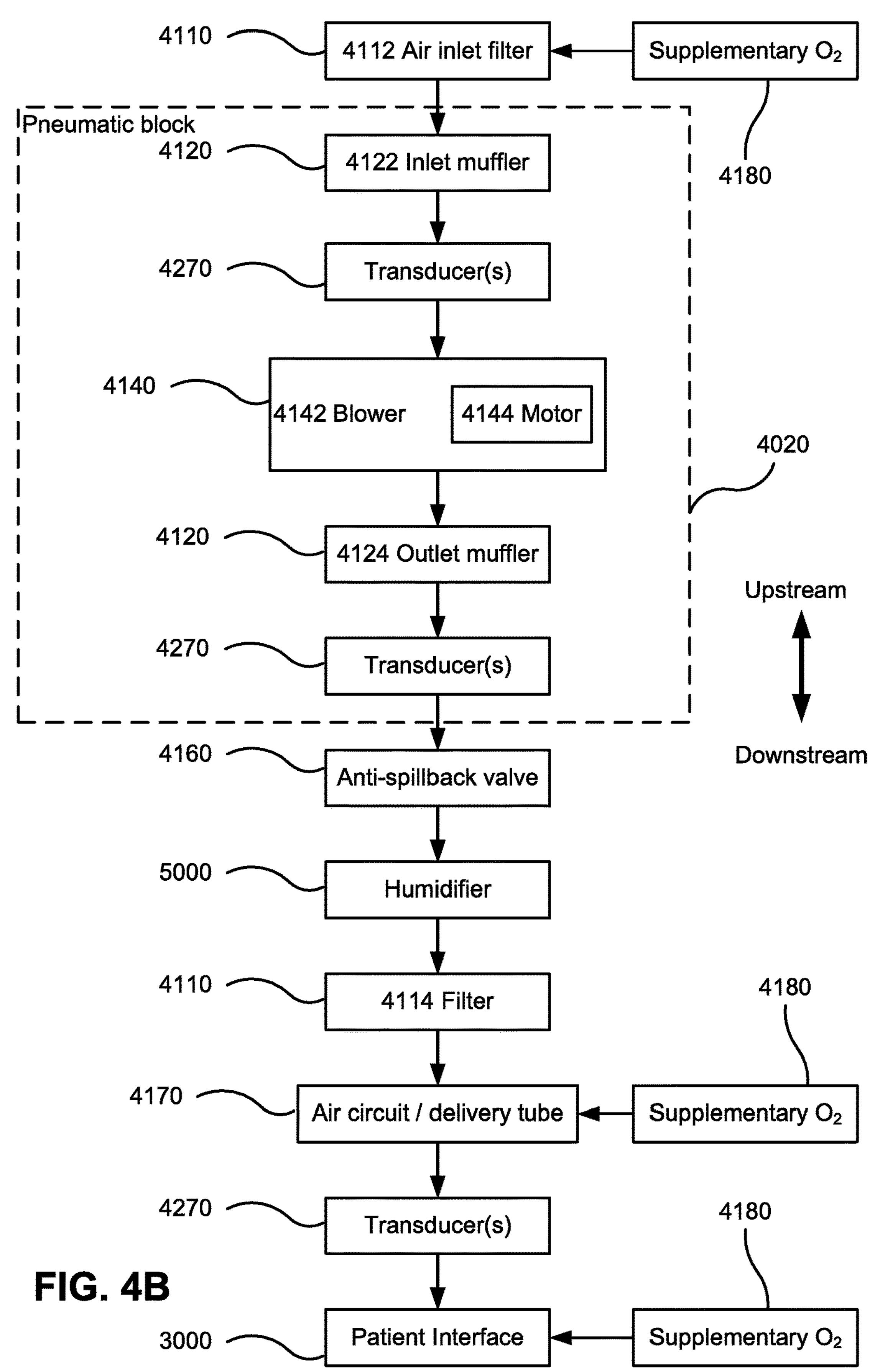
Figure 4C:
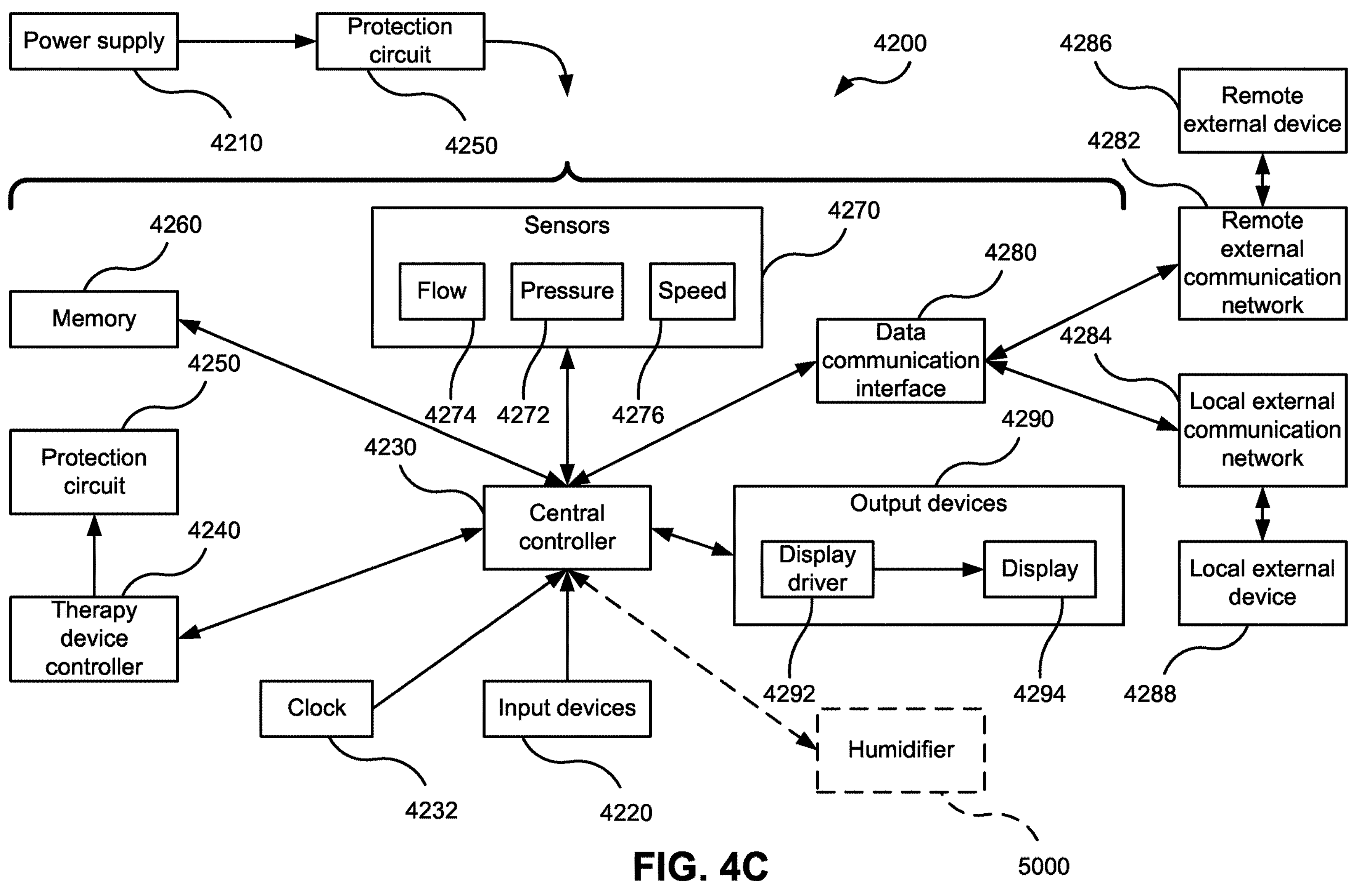
Figure 4D:
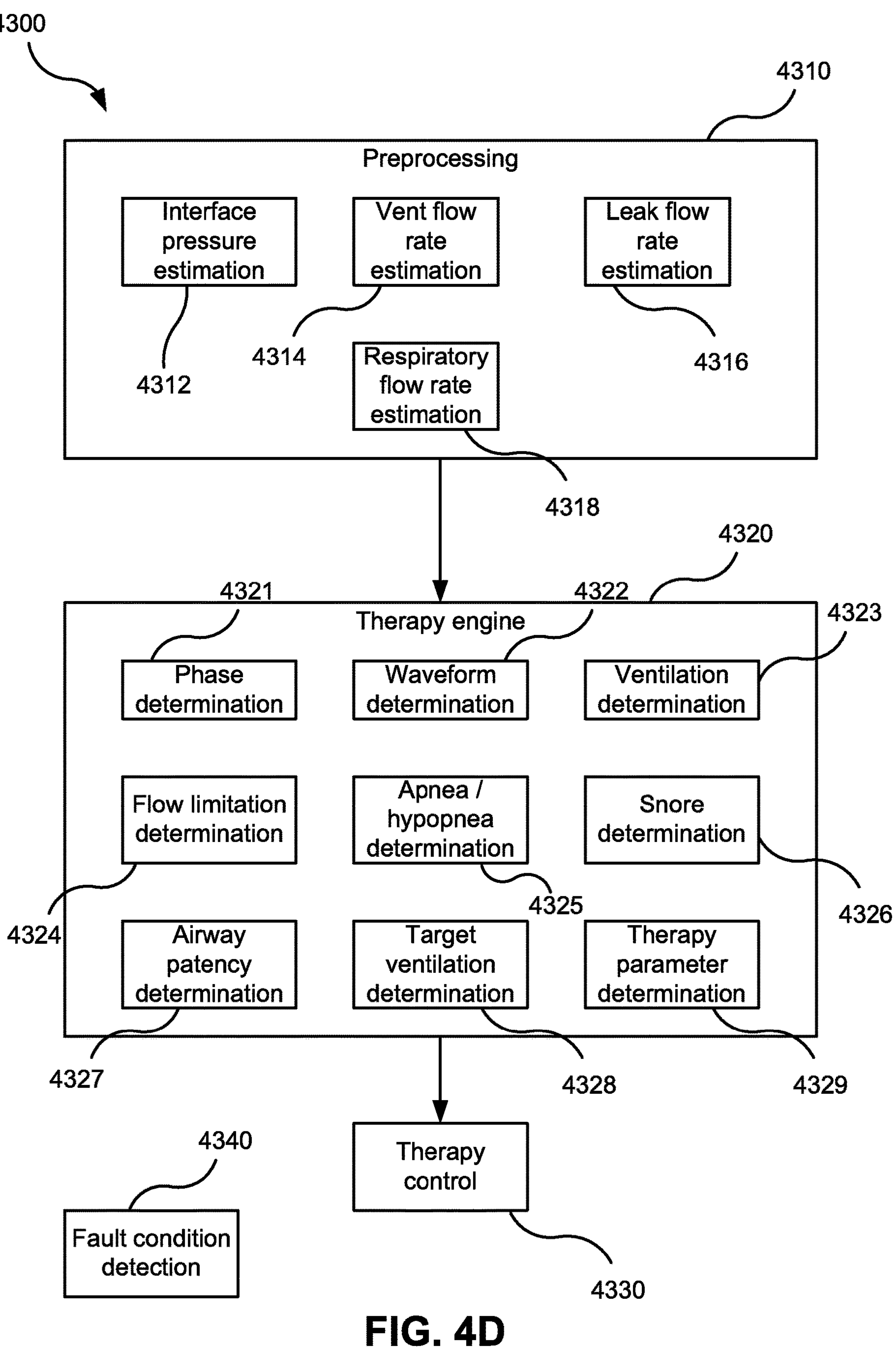
Figure 4E:
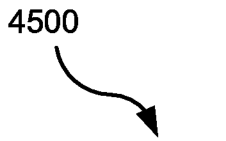
Figure 4E:
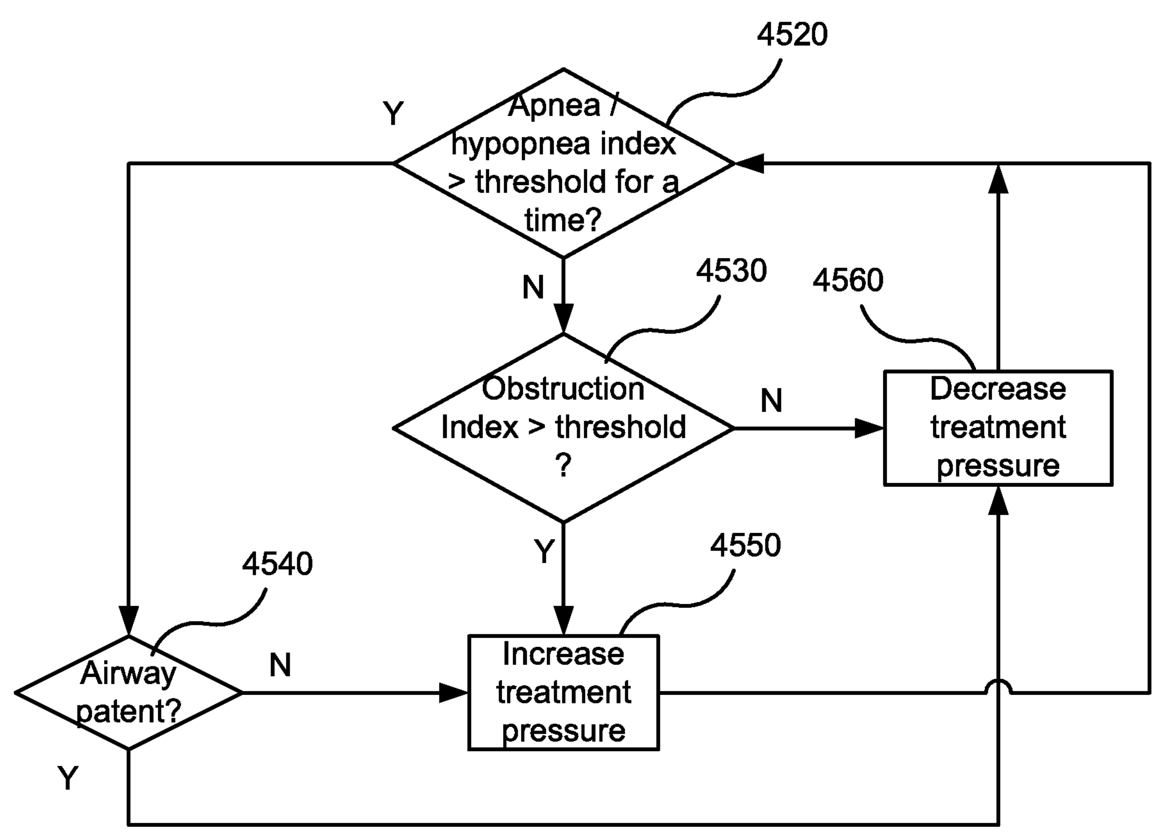

FIG. 4E is a flow chart illustrating a method 4500 carried out by the central controller 4230 to continuously compute the base pressure $P_0$ as part of an APAP therapy implementation of the therapy parameter determination algorithm 4329, when the pressure support A is identically zero.

The method 4500 starts at step 4520, at which the central controller 4230 compares the measure of the presence of apnea/hypopnea with a first threshold, and determines whether the measure of the presence of apnea/hypopnea has exceeded the first threshold for a predetermined period of time, indicating an apnea/hypopnea is occurring. If so, the method 4500 proceeds to step 4540; otherwise, the method 4500 proceeds to step 4530. At step 4540, the central controller 4230 compares the measure of airway patency with a second threshold. If the measure of airway patency exceeds the second threshold, indicating the airway is patent, the detected apnea/hypopnea is deemed central, and the method 4500 proceeds to step 4560; otherwise, the apnea/hypopnea is deemed obstructive, and the method 4500 proceeds to step 4550.

At step 4530, the central controller 4230 compares the measure of flow limitation with a third threshold. If the measure of flow limitation exceeds the third threshold, indicating inspiratory flow is limited, the method 4500 proceeds to step 4550; otherwise, the method 4500 proceeds to step 4560.

At step 4550, the central controller 4230 increases the base pressure $P_0$ by a predetermined pressure increment $\Delta P$, provided the resulting treatment pressure Pt would not exceed a maximum treatment pressure Pmax. In one implementation, the predetermined pressure increment $\Delta P$ and maximum treatment pressure Pmax are 1 $cmH_2O$ and 25 $cmH_2O$ respectively. In other implementations, the pressure increment $\Delta P$ can be as low as 0.1 $cmH_2O$ and as high as 3 $cmH_2O$, or as low as 0.5 $cmH_2O$ and as high as 2 $cmH_2O$. In other implementations, the maximum treatment pressure Pmax can be as low as 15 $cmH_2O$ and as high as 35 $cmH_2O$, or as low as 20 $cmH_2O$ and as high as 30 $cmH_2O$. The method 4500 then returns to step 4520.

At step 4560, the central controller 4230 decreases the base pressure $P_0$ by a decrement, provided the decreased base pressure $P_0$ would not fall below a minimum treatment pressure Pmin. The method 4500 then returns to step 4520. In one implementation, the decrement is proportional to the value of $P_0$–Pmin, so that the decrease in $P_0$ to the minimum treatment pressure Pmin in the absence of any detected events is exponential. In one implementation, the constant of proportionality is set such that the time constant $\tau$ of the exponential decrease of $P_0$ is 60 minutes, and the minimum treatment pressure Pmin is 4 $cmH_2O$. In other implementations, the time constant r could be as low as 1 minute and as high as 300 minutes, or as low as 5 minutes and as high as 180 minutes. In other implementations, the minimum treatment pressure Pmin can be as low as 0 $cmH_2O$ and as high as 8 $cmH_2O$, or as low as 2 $cmH_2O$ and as high as 6 $cmH_2O$. Alternatively, the decrement in $P_0$ could be predetermined, so the decrease in $P_0$ to the minimum treatment pressure Pmin in the absence of any detected events is linear.

4.9.2 Bi-Level Therapy

In other implementations of this form of the present technology, the value of amplitude A in equation (1) may be positive. Such implementations are known as bi-level therapy, because in determining the treatment pressure Pt using equation (1) with positive amplitude A, the therapy parameter determination algorithm 4329 oscillates the treatment pressure Pt between two values or levels in synchrony with the spontaneous respiratory effort of the patient 1000. That is, based on the typical waveform templates $\Pi(\Phi, t)$ described above, the therapy parameter determination algorithm 4329 increases the treatment pressure Pt to $P_0$+A (known as the IPAP) at the start of, or during, or inspiration and decreases the treatment pressure Pt to the base pressure $P_0$ (known as the EPAP) at the start of, or during, expiration.

In some forms of bi-level therapy, the IPAP is a treatment pressure that has the same purpose as the treatment pressure in CPAP therapy modes, and the EPAP is the IPAP minus the amplitude A, which has a "small" value (a few $cmH_2O$) sometimes referred to as the Expiratory Pressure Relief (EPR). Such forms are sometimes referred to as CPAP therapy with EPR, which is generally thought to be more comfortable than straight CPAP therapy. In CPAP therapy with EPR, either or both of the IPAP and the EPAP may be constant values that are hard-coded or manually entered to the RPT device 4000. Alternatively, the therapy parameter determination algorithm 4329 may repeatedly compute the IPAP and/or the EPAP during CPAP with EPR. In this alternative, the therapy parameter determination algorithm 4329 repeatedly computes the EPAP and/or the IPAP as a function of indices or measures of sleep disordered breathing returned by the respective algorithms in the therapy engine module 4320 in analogous fashion to the computation of the base pressure $P_0$ in APAP therapy described above.

In other forms of bi-level therapy, the amplitude A is large enough that the RPT device 4000 does some or all of the work of breathing of the patient 1000. In such forms, known as pressure support ventilation therapy, the amplitude A is referred to as the pressure support, or swing. In pressure support ventilation therapy, the IPAP is the base pressure $P_0$ plus the pressure support A, and the EPAP is the base pressure $P_0$.

In some forms of pressure support ventilation therapy, known as fixed pressure support ventilation therapy, the pressure support A is fixed at a predetermined value, e.g. 10 $cmH_2O$. The predetermined pressure support value is a setting of the RPT device 4000, and may be set for example by hard-coding during configuration of the RPT device 4000 or by manual entry through the input device 4220.

In other forms of pressure support ventilation therapy, broadly known as servo-ventilation, the therapy parameter determination algorithm 4329 takes as input some currently measured or estimated parameter of the respiratory cycle (e.g. the current measure Vent of ventilation) and a target value of that respiratory parameter (e.g. a target value Vtgt of ventilation) and repeatedly adjusts the parameters of equation (1) to bring the current measure of the respiratory parameter towards the target value. In a form of servo-ventilation known as adaptive servo-ventilation (ASV), which has been used to treat CSR, the respiratory parameter is ventilation, and the target ventilation value Vtgt is computed by the target ventilation determination algorithm 4328 from the typical recent ventilation Vtyp, as described above.

In some forms of servo-ventilation, the therapy parameter determination algorithm 4329 applies a control methodology to repeatedly compute the pressure support A so as to bring the current measure of the respiratory parameter towards the target value. One such control methodology is Proportional-Integral (PI) control. In one implementation of PI control, suitable for ASV modes in which a target ventilation Vtgt is set to slightly less than the typical recent ventilation Vtyp, the pressure support A is repeatedly computed as:

$$A = G\int(\text{Vent} - Vtgt)dt \tag{2}$$

where G is the gain of the PI control. Larger values of gain G can result in positive feedback in the therapy engine module 4320. Smaller values of gain G may permit some residual untreated CSR or central sleep apnea. In some implementations, the gain G is fixed at a predetermined value, such as −0.4 $cmH_2O$/(L/min)/sec. Alternatively, the gain G may be varied between therapy sessions, starting small and increasing from session to session until a value that substantially eliminates CSR is reached. Conventional means for retrospectively analysing the parameters of a therapy session to assess the severity of CSR during the therapy session may be employed in such implementations In yet other implementations, the gain G may vary depending on the difference between the current measure Vent of ventilation and the target ventilation Vtgt.

Other servo-ventilation control methodologies that may be applied by the therapy parameter determination algorithm 4329 include proportional (P), proportional-differential (PD), and proportional-integral-differential (PID).

The value of the pressure support A computed via equation (2) may be clipped to a range defined as [Amin, Amax]. In this implementation, the pressure support A sits by default at the minimum pressure support Amin until the measure of current ventilation Vent falls below the target ventilation Vtgt, at which point A starts increasing, only falling back to Amin when Vent exceeds Vtgt once again.

The pressure support limits Amin and Amax are settings of the RPT device 4000, set for example by hard-coding during configuration of the RPT device 4000 or by manual entry through the input device 4220.

In pressure support ventilation therapy modes, the EPAP is the base pressure $P_0$. As with the base pressure $P_0$ in CPAP therapy, the EPAP may be a constant value that is prescribed or determined during titration. Such a constant EPAP may be set for example by hard-coding during configuration of the RPT device 4000 or by manual entry through the input device 4220. This alternative is sometimes referred to as fixed-EPAP pressure support ventilation therapy. Titration of the EPAP for a given patient may be performed by a clinician during a titration session with the aid of PSG, with the aim of preventing obstructive apneas, thereby maintaining an open airway for the pressure support ventilation therapy, in similar fashion to titration of the base pressure $P_0$ in constant CPAP therapy.

Alternatively, the therapy parameter determination algorithm 4329 may repeatedly compute the base pressure $P_0$ during pressure support ventilation therapy. In such implementations, the therapy parameter determination algorithm 4329 repeatedly computes the EPAP as a function of indices or measures of sleep disordered breathing returned by the respective algorithms in the therapy engine module 4320, such as one or more of flow limitation, apnea, hypopnea, patency, and snore. Because the continuous computation of the EPAP resembles the manual adjustment of the EPAP by a clinician during titration of the EPAP, this process is also sometimes referred to as auto-titration of the EPAP, and the therapy mode is known as auto-titrating EPAP pressure support ventilation therapy, or auto-EPAP pressure support ventilation therapy.

4.9.3 High Flow Therapy

In other forms of respiratory therapy, the pressure of the flow of air is not controlled as it is for respiratory pressure therapy. Rather, the central controller 4230 controls the pressure generator 4140 to deliver a flow of air whose device flow rate Qd is controlled to a treatment or target flow rate Qtgt. Such forms are generally grouped under the heading of flow therapy. In flow therapy, the treatment flow rate Qtgt may be a constant value that is hard-coded or manually entered to the RPT device 4000. If the treatment flow rate Qtgt is sufficient to exceed the patient's peak inspiratory flow rate, the therapy is generally referred to as high flow therapy (HFT). Alternatively, the treatment flow rate may be a profile Qtgt(t) that varies over the respiratory cycle.

4.10 Data Transmission

FIG. 8 shows a block diagram illustrating one implementation of an RPT system according to the present technology. The RPT system comprises an RPT device 4000 configured to provide respiratory pressure therapy to a patient 1000, a data server 7100, and a patient computing device 7050 associated with the patient 1000. The patient computing device 7050 is co-located with the patient 1000 and the RPT device 4000. In the implementation shown in FIG. 8, the RPT device 4000, the patient computing device 7050, and the data server 7100 are connected to a wide area network 7090 such as an internet, intranet, the cloud, or the Internet. The connections to the network may be wired or wireless. The network may be identified with the remote external communication network 4282 of FIG. 4C, and the data server 7100 may be identified with the remote external device 4286 of FIG. 4C. The patient computing device 7050 may be a personal computer, mobile phone, tablet computer, or other device. The patient computing device 7050 is configured to intermediate between the patient 1000 and the data server 7100 over the wide area network 7090. In one implementation, this intermediation is performed by a software application program 7060 that runs on the patient computing device 7050. The patient program 7060 may be a dedicated application referred to as a "patient application" that interacts with a complementary process hosted by the data server 7100. In another implementation, the patient program 7060 is a web browser that interacts via a secure portal with a web site hosted by the data server 7100. In yet another implementation, the patient program 7060 is an email client.

In other examples, the RPT device 4000 communicates with the patient computing device 7050 via a local (wired or wireless) communications protocol such as a local network protocol (e.g., Bluetooth). In the alternative implementation, the local network may be identified with the local external communication network 4284 of FIG. 4C, and the patient computing device 7050 may be identified with the local external device 4288 of FIG. 4C. In the alternative implementation, the patient computing device 7050, via the patient program 7060, is configured to intermediate between the patient 1000 and the data server 7100, over the network 7090, and also between the RPT device 4000 and the data server 7100 over the network 7090.

The RPT system may contain other RPT devices (not shown) associated with respective patients who also have respective associated computing devices. Further, the RPT system 7000 may include other monitoring or therapy devices that may be interfaced with the controller 4230 or the patient computing device 7050. All the patients in the RPT system 7000 are managed by the data server 7100.

The RPT device 4000 is configured to store in the memory 4260 therapy data from each RPT session delivered to the patient 1000. Therapy data for an RPT session comprises the settings of the RPT device 4000 and therapy variable data representing one or more variables of the respiratory pressure therapy throughout the RPT session.

The data server 7100 may also be configured to receive data from the patient computing device 7050. Such may include data entered by the patient 1000 to the patient program 7060, or therapy/usage data in the alternative implementation 7000B described above.

The data server 7100 is also configured to transmit electronic messages to the patient computing device 7050. The messages may be in the form of emails, SMS messages, automated voice messages, or notifications within the patient program 7060.

The RPT device 4000 may be configured such that its therapy mode, or settings for a particular therapy mode, may be altered on receipt of a corresponding command via its wide area or local area network connection. In such an implementation, the data server 7100 may also be configured to send such commands directly to the RPT device 4000 (in the implementation 7000) or indirectly to the RPT device 4000, relayed via the patient computing device 7050 (in the implementation 7000B).

The server 7100 and database 7200 may be a single server and database combination or may contain multiple combinations of servers 7100 and databases 7200 at different locations. For instance, the RPT devices 4000 may be connected to one or more server 7100 and database 7200 combinations that store and communicate various data features, including therapy settings or parameters, and other data over network 7090.

For instance, the system may include a general patient system 8100 and a prescription system 8200 that each includes a server 7100 and database 7200 combination. In this example, the prescription system 8200 may store prescriptions of patients 1000 referenced to a unique identifier for the patient 1000. The prescription data stored in the database 7200 may include data representing the prescribed pressure levels (e.g. mix and man pressures), modes of therapy, and other respiratory therapy parameters.

In some examples, additional data and preferences relevant to the patient's therapy that does not include the patient's prescribed therapy parameters may be stored on the general patient system 8100 (rather than the prescription system 8200) on the associated database 7200. For instance, the patients 1000 profile data, other preferences, account information, etc. may all be stored on a separate database 7200. This may be advantageous because any database 8200 and system that includes data that indicates the physician's prescribed therapy parameters may be required to be compliant with privacy laws and/or comply with certain regulations. Thus, by storing the non-prescribed settings on general patient system 8100, it may not be required to comply with as many regulations. In other examples, both prescription and non-prescription related parameters are stored on the same server 7100 and database 7200.

Therapy Settings

In general, therapy settings stored on a database 7200 may include data representing the treatment pressure Pt which may be implemented by the controller 4230 which sets the pressure using different therapy parameter determination algorithms 4329. In some cases, the treatment pressure may include a minimum and maximum pressure. The therapy settings may also include a constant pressure for CPAP, or the therapy system may provide APAP therapy by computing a base pressure based on the treatment pressure and various indices as described above.

The therapy settings may include various modes including CPAP, APAP, Bi-Level Therapy, High Flow Therapy, and others. Additionally, therapy settings may include humidification or temperature settings, and other features or characteristics of the respiratory therapy that may be controlled or manipulated.

The therapy settings may be stored in a database 7200 referenced to a patient 1000 (e.g. through a unique identifier) and may also reference the type and or model number of respiratory therapy device 4000 for which the therapy settings are valid. In some examples, the prescription settings that include the treatment pressure may also be referenced to: (1) a date of prescription, (2) a prescribing doctor, (3) a prescribed mode of therapy, (4) a prescribed type, model, and serial number of respiratory therapy device 4000, and (5) other information.

4.11 Transferring Therapy Settings

One form of the present technology comprises methods and systems for automatically porting respiratory therapy settings to a new respiratory therapy device 4000. Currently, when patient 1000 receives a replacement respiratory therapy device 4000, an upgraded respiratory therapy device 4000, or an additional or new type of respiratory therapy device 4000, the prescription settings must be manually ported, with human intervention. For instance, to acquire a new RPT device 4000 when patient 1000 already has an existing device and prescription (REPAP), the patient 1000 must order the new device from a provider, which must install the settings manually on the RPT device 4000 or the provider may manually update their database 7200 through the server 7100 to add the new RPT device 4000. This includes adding its model number, network address, and prescription therapy settings that are compatible with that RPT device 4000. Therefore, patient 1000 may be limited to ordering a new device from a current provider without facing difficulties or an extended installation process.

Accordingly, the inventors have developed new technology to automatically port the respiratory therapy settings to the new RPT device 4000. This is very advantageous, because it provides an opportunity to purchase a RPT device 4000 from any vendor without having the prescription therapy settings preinstalled or the unit pre-registered with the provider's server 7100 and database 7200. Accordingly, this makes ordering and installation of a new RPT device 4000 automatic, and require little human intervention.

Additionally, the inventors have developed a number of features to implement this technology, which include:

(1) translation of therapy settings to different types or models of RPT devices 4000

(2) processes to determine whether a prescription is valid;

(3) processes to determine whether a prescription is effective;

(4) processes to validate the identity of the patient 1000 and determine whether the patient 1000 is in possession of an existing RPT device 4000.

(5) processes to validate other patient 1000 data and identify changes to the patient 1000 data that may require a new prescription;

(6) monitoring of the RPT device 4000 therapy quality indicators after porting therapy settings to determine whether the prescription is adequate on the new RPT device 4000; and (7) others.

These new features are described herein in some examples. The technology may incorporate various combinations of these features.

FIG. 9 shows a flow diagram of one method of transferring therapy settings to a new RPT device 4000. First, the system may receive a request 9000 to port therapy settings to a new RPT device 4000. This may be through a patient computing device 7050, through an interface 4229 on a new RPT device 4000, or other computing device. In some examples, the new RPT device 4000 will be locked until receiving new settings from the cloud, including for instance, with a key to unlock the device for use. This allows the device to be shipped to a patient without settings already set based on the patient's prescription. And may even enable different labelling or regulatory requirements for certain products in the future.

In some examples, the patient 1000 may log into an account on their patient computing device 7050 using a unique user ID and password 9100 and indicate through an interface that they have received an additional RPT device 4000 and they would like to port settings. In other examples, once the patient 1000 powers on the new RPT device 4000, the new device may request account information or otherwise initiate a therapy settings porting process.

In some examples, the patient computing device 7050 or other computing device may request the serial number of the replacement RPT device 9200. In other examples, the computing device may send a request for the serial number of the existing RPT device 9200 to ensure the patient 1000 is in possession of the device. In other examples, the existing RPT device 4000 may display a new and unique code on the display 4294 the patient 1000 must enter into the patient computing device 7050 or other computing device, to ensure they are currently in possession of the existing RPT device 4000 associated with their account.

In one example, one of the servers 7100 and database 7200 may check the information including the serial numbers or code to determine in matches information associated with the patient ID stored in the database 7200.

Next, the server 7100 will send the prescription therapy settings to the RPT device 4000 if the information is validated 9300 and they will be stored in the new RPT device's 4000 memory. Various methods could be utilized to transfer the settings to the new RPT device 4000, including porting the settings over a Bluetooth connection 9450 between the patient computing device 7050 and the new RPT device 4000. In this example, the patient computing device 7050 may have a patient account that is logged in, and then establish a connection to the new RPT device 4000 through Bluetooth. In other examples, the settings data could be sent over a cellular network to the RPT device's 4000 cellular antenna 9460, or over a Wi-Fi connection 9470 to the new RPT device 4000. In some examples, the settings will be sent encrypted from the server 7100 to the RPT device 4000 using the patient computing device 7050 as a conduit over Bluetooth. In this example, the patient computing device 7050 would not be able to decipher or store the settings, and rather the settings would be sent encrypted from at least one of the servers 7100 to the new RPT device 4000.

Therapy Settings Porting Translation and Validation Processes

FIG. 10 shows a block diagram illustrating one implementation of an RPT system according to the present technology. In this example, the technology includes a prescription settings translator 10020 and portability check 10030 programs that reside on one of the database 7200 and server 7100 combinations or reside on the RPT device 4000 or patient computing device 7050. The check 10030 and translator 10020 programs are utilized to process the prescription therapy settings 10060 and any other general patient data 10050, preferences or other information that needs to be ported to the new RPT device 4000.

FIG. 11 illustrates an example method of implementing the translations and checks. For instance, in some examples, and with reference to FIG. 9, once the serial number and account ID are validated 9100 and 9200, the technology may perform checks and translations before paring therapy settings 11400.

Therapy Settings Porting Validation Processes

The system may perform the following checks 11400 or validation processes, and if any of them fail, the patient 1000 may be flagged for follow up and the settings will not be ported 11400:

(1) valid prescription;
(2) prescription date;
(3) patient data change;
(4) therapy quality indicators;
(5) oximeter readings 11460; and
(6) others.

For instance, the before the server 7100 sends the prescription therapy settings, comfort settings or other settings, the technology may perform checks of various data, including data output from the RPT device 4000 to ensure that the therapy settings should be ported. If the server 7100 determines any of the checks failed, the server 7100 will send a response to the new RPT device 4000 or patient computing device 7050 indicating that the therapy settings could not be ported and the patient 1000 has been flagged for follow up to receive an updated prescription.

For example, a date associated with the current prescription therapy settings (e.g. a time stamp of the date a prescription was entered, written, or received in the database 7200) may be checked against a current date to ensure a threshold amount of time hasn't passed, for instance, one year, two years, 5 years etc. since the prescription was first entered or prescribed. This would prevent the patient 1000 from continually using the prescription that may have expired, or that the patient risks a denial or delay with their insurance provider or payer, due to an out-of-date prescription.

Additionally, patient data changes 11480 may be evaluated to determine whether there are any significant changes to the patient 1000 that are associated with a change in prescription. For instance, the system may check the patient's 1000 age based on their profile data to determine whether a patient 1000 has reached any milestones in age where therapy settings generally need to be updated, due to changing physiology associated with aging. This could be checked by checking the birthdate on the patient's 1000 profile data 10050 stored on a general patient system 8100, and comparing it to the current date.

Furthermore, patient data changes 11480 could be information or data acquired by sending a questionnaire to a patient interface (on any of the various computing devices or RPT device input 4220) when initiation of the porting of settings has begun. For instance, the questionnaire could ask the patient 1000 questions to assess:

(1) weight;
(2) BMI;
(3) Subjective sleep quality;
(4) Mattress or other sleep environment changes;
(5) Moving residences; and
(6) Other information.

For instance, if it is determined that a patient's 1000 weight or BMI has changed over a threshold amount, the pressure may need to be evaluated based on known threshold changes of BMI or a patient's 1000 position on a weight or BMI curve (given their gender, ethnicity etc.) that require a new pressure or other therapy parameter changes. Additionally, other factors that may impact settings may be inquired.

In some examples, these factors may automatically be assessed using various image or other data processing techniques to estimate relevant characteristics of a patient 1000. For instance, a selfie tool could process an image of the patient 1000 and compare it to a previous image of the patient 1000 to determine whether the change in image indicates a change in BMI. This may include a method of relative sizing of the patient 1000, including by measuring a diameter of an eye feature like a pupil or iris, that will not change over time. Additionally, the selfie tool may also utilize measurement of the eye feature to determine the relative sizes (e.g. compensate for scale based on differences in distance of the camera from the face between images.

In some examples, the selfie tool may require the patient 1000 to move the camera closer to the patient's 1000 face until the eye measurement (or other common feature) determines the patient 1000 has the camera at an acceptable distance, predetermined distance, or the same distance as in a prior image. In some examples, the camera may include depth sensor technology, that may provide improved estimation of the changes of the patient's face that would be relevant to therapy changes.

In some examples, the technology my first check indicators of therapy quality before porting the therapy settings. For instance, if the therapy quality indicators are below an acceptable threshold or indicate there is an issue with the patient's 1000 therapy, the technology may deny porting of the settings 11500 and flag the patient for follow up. Therapy quality indicators may include:

(1) usage data output from the RPT device 4000—usage patterns may indicate the patient's 1000 prescription or other settings are causing the patient 1000 to discontinue or minimize use;
(2) therapy quality indexes;
(3) hypopnea events;
(4) other sleep disturbances;
(5) sleep scores;
(6) data output from a pulse oximeter; and
(7) others.

In some examples, the technology my present questions to the patient 1000 to determine or assess if they will be able to handle a switch to a new RPT device 4000 without a physician's assessment and prescription. For instance, if a patient 1000 desires to switch from a full mask to a nose only mask, the technology may request to take a picture to assess their nose region, or process audio data of the patient 1000 sleeping to determine whether they are a mouth or nose breather. In those cases, the technology may automatically deny porting settings 11500 if there are any issues.

Additionally, the technology may additionally check the same therapy quality indicators a certain time period after initiation of use of the new RPT device 4000, to provide an initial check on the patient's 1000 quality using the same parameters on the replacement RPT device 4000. This may include a time window of 1 day, 2 days, 1 week, a month or other suitable time periods. Accordingly, the technology may check for a baseline level of respiratory therapy quality or a threshold decrease amount of respiratory therapy quality compared to the respiratory therapy quality on the current respiratory therapy device 4000.

Settings Translator

In addition to flagging for issues prior to porting therapy settings, the technology may also translate, calibrate or adjust settings for a new unit, model, or type of respiratory therapy device 4000. The prescription settings translator 10020 may include a variety of features to map, translate, calibrate or otherwise adapt settings from a current RPT device 4000 to a new device 4000.

For instance, a database 7200 may include a mapping between models, types, and units of RPT devices 4000. For instance, a therapy pressure may be slightly adjusted to compensate for differences in pressure experienced between certain units. This may include a listing and mapping on a database spreadsheet or other ontology to map units together, and equations for converting the pressures or other modes and settings to a form for the new device.

Additionally, non-prescription settings, modes, and other features may be adjusted by known calibration amounts between devices. For instance, the intensity of the RAMP feature, or the rate of increase and/or decrease of pressure in an auto-titrating algorithm could be changed between different models types of devices if it is known that certain models have slightly greater pressure, or patients respond better to lower pressures, for instance.

In some examples, the technology may learn over time to map, including non-prescription features, between units based on patients post use adjustment of these features. Accordingly, the technology may be able to predict the mappings between units for particular types of patients based on the patient data and background.

4.12 Glossary

For the purposes of the present technology disclosure, in certain forms of the present technology, one or more of the following definitions may apply. In other forms of the present technology, alternative definitions may apply.

4.12.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Device flow rate, Qd, is the flow rate of air leaving the RPT device. Total flow rate, Qt, is the flow rate of air and any supplementary gas reaching the patient interface via the air circuit. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, g-f/$cm^2$ and hectopascal. 1 $cmH_2O$ is equal to 1 g-f/$cm^2$ and is approximately 0.98 hectopascal (1 hectopascal=100 Pa=100 N/$m^2$=millibar ~0.001 atm). In this specification, unless otherwise stated, pressure is given in units of $cmH_2O$.

The pressure in the patient interface is given the symbol Pm, while the treatment pressure, which represents a target value to be achieved by the interface pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

4.12.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker.

Polycarbonate: a thermoplastic polymer of Bisphenol-A Carbonate.

4.12.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

(i) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) lime (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

4.12.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired interface pressure which the ventilator will attempt to achieve at a given time.

End expiratory pressure (EEP): Desired interface pressure which the ventilator will attempt to achieve at the end of the expiratory portion of the breath. If the pressure waveform template $\Pi(\Phi)$ is zero-valued at the end of expiration, i.e. $\Pi=0$ when $\Phi=1$, the EEP is equal to the EPAP.

Inspiratory positive airway pressure (IPAP): Maximum desired interface pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

4.13 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

The invention claimed is:

1. A system comprising:

a prescription database with prescription therapy settings referenced to patient account IDs comprising a unique identifier for each patient in the database in communication with a prescription server;

a first respiratory therapy device;

a second respiratory therapy device;

an interface;

a memory containing machine readable medium comprising machine executable code having stored thereon instructions for performing a method;

a control system coupled to the memory comprising one or more processors, the control system configured to execute the machine executable code to cause the control system to:

receive input, from the interface, indicating a patient would like to port prescription therapy settings for the first respiratory therapy device from the first respiratory therapy device to the second respiratory therapy device;

receive, through the interface, an account ID associated with the patient, a hardware identifier associated with the first respiratory therapy device, and a hardware identifier associated with the second respiratory therapy device;

send, to the prescription server, a request comprising the account ID and the hardware identifier associated with the first respiratory therapy device to retrieve the prescription therapy settings for the first respiratory therapy device from the prescription server;

receive, from the prescription server based on the account ID, the prescription therapy settings for the first respiratory therapy device if the hardware identifier is validated; and store the prescription therapy settings for the first respiratory therapy device in a memory of the second respiratory therapy device.

2. The system of claim 1, wherein the receiving, from the prescription server, prescription therapy settings further comprises:

retrieving a respiratory quality indicator referenced to the account ID based on respiratory therapy data output from the first respiratory device;

determining whether the respiratory quality indicator is above a threshold; and flagging the patient for follow up and denying the request to port the prescription therapy settings if the respiratory quality indicator is below the threshold.

3. The system of claim 2, wherein the respiratory quality indicator is an apnea hypopnea index.

4. The system of claim 1, wherein the receiving, from the prescription server, prescription therapy settings further comprises:

determining a time window that has expired since the prescription therapy settings were last updated;

determining whether the time window is above a threshold; and flagging the patient for follow up in a prescription therapy database and denying the request to port the prescription therapy settings if the time window is above the threshold.

5. The system of claim 1, wherein the receiving, from the prescription server, prescription therapy settings further comprises:

requesting a set of information from the patient;

evaluating the information to determine whether a significant change has occurred relevant to the patient prescription therapy settings; and flagging the patient for follow up in a prescription therapy database and denying the request to port the prescription therapy settings if the significant change has occurred.

6. The system of claim 5, wherein the set of information includes weight, BMI, muscle tone changes, or any combination thereof.

7. The system of claim 5, wherein the set of information comprises audio data received through a microphone, and wherein the audio data is processed to determine whether the patient has a significant change in tone.

8. The system of claim 5, wherein the set of information comprises image data of a face that is compared to previously captured image data to identify a significant facial change.

9. The system of claim 8, wherein the significant facial change indicates a significant change in BMI.

10. The system of claim 1, wherein the receiving, from the prescription server, prescription therapy settings further comprises:

requesting a set of oximeter data output from a pulse oximeter;

processing the oximeter data to determine whether the prescription therapy settings should be updated; and flagging the patient for follow-up in the prescription therapy database and denying the request to port the prescription therapy settings if the settings should not be updated.

11. The system of claim 1, wherein the prescription therapy settings are received over a cellular antenna connected to the first respiratory therapy device.

12. The system of claim 1, wherein the prescription therapy settings are received over a Bluetooth or Wi-Fi connection to a mobile device connected to the first respiratory therapy device.

13. The system of claim 1, wherein the prescription therapy settings are encrypted from the prescription server to the first respiratory therapy device.

14. The system of claim 1, wherein the prescription therapy settings comprise minimum pressure, maximum pressure, and a therapy mode.

15. The system of claim 1, wherein the receiving, through the interface, an account ID associated with the patient's account and a serial number associated with the second respiratory therapy device, further comprises:

displaying a code on a display of the first respiratory therapy device;

requesting, on the interface, the code to be entered; and only receiving the general and prescription therapy settings of the code is validated.

16. The system of claim 1, wherein the receiving the prescription therapy settings further comprises translating the prescription therapy settings by a predetermined translation factor based on a difference between the first and second respiratory therapy device.

17. A system comprising:

a prescription database with prescription therapy settings referenced to patient prescription IDs comprising a unique identifier for each patient in the database in communication with a prescription server;

a patient database with general patient data referenced to a set of patient account IDs in communication with a patient server;

a first respiratory therapy device;

an interface;

a memory containing machine readable medium comprising machine executable code having stored thereon instructions for performing a method;

a control system coupled to the memory comprising one or more processors, the control system configured to execute the machine executable code to cause the control system to:

receive input, from the interface, indicating a patient would like to port prescription therapy settings from a second respiratory therapy device;

receiving, through the interface, an account ID associated with the patient and a serial number associated with the second respiratory therapy device;

sending, to the patient server, a request comprising the account ID and the serial number to retrieve the prescription therapy settings for the second respiratory therapy device from the prescription server;

receiving, from the patient server based on the prescription ID, prescription therapy settings for the second respiratory therapy device if the serial number is validated set from the prescription server; and storing the prescription therapy settings for the second respiratory therapy device in a memory of the first respiratory therapy device.

18. The system of claim 17, wherein storing the prescription therapy settings in a memory of the second respiratory therapy device further comprises storing the prescription therapy settings for a single usage session.

19. The system of claim 18, wherein the single usage session comprises deleting the prescription therapy settings in the memory of the second respiratory therapy device after a certain time window has expired.

20. The system of claim 18, wherein the single usage session comprises deleting the prescription therapy settings in the memory of the second respiratory therapy device after the respiratory therapy device has been powered off.

21. The system of claim 18, wherein the single usage session comprises deleting the prescription therapy settings in the memory of the second respiratory therapy device after 24 hours.

22. The system of claim 18, wherein the single usage session comprises deleting the prescription therapy settings in the memory of the second respiratory therapy device after a notification that the patient has checked out of an associated hotel.

23. A method comprising:

receiving, at a prescription server from a patient computing device, a request to port prescription therapy settings to a respiratory therapy device comprising an account ID associated with the patient and a serial number associated with the respiratory therapy device;

receiving at the prescription server, a query for a prescription database for the account ID and the serial number to retrieve a set of prescription therapy settings from the prescription database;

processing, with the prescription server, the serial number to determine whether it is validly associated with the account ID; and sending, to the respiratory therapy device, the set of prescription therapy settings referenced to the account ID if the serial number is validated.

24. The method of claim 23, wherein the prescription therapy settings include treatment pressure referenced to a date of prescription, a prescribing doctor, a prescribed mode of therapy, a prescribed type, model, and serial number of respiratory therapy device, or any combination thereof.

25. The method of claim 23, further comprising determining whether the prescription is adequate on the respiratory therapy device.

26. The method of claim 25, further comprising determining a new prescription is required for the patient, if the prescription is not adequate on the respiratory therapy device.

27. The method of claim 23, further comprising determining whether the patient is in possession of the respiratory therapy device.

28. The method of claim 23, further comprising adjusting the prescription therapy settings from another respiratory therapy device currently being used by the patient to the respiratory therapy device.

29. The method of claim 23, wherein the prescription server is configured to predict mappings between respiratory therapy devices for particular types of patients based on patient data.

* * * * *